United States Patent
Saward et al.

(10) Patent No.: US 9,751,919 B2
(45) Date of Patent: Sep. 5, 2017

(54) ANTIMICROBIAL COMPOSITIONS COMPRISING A HYALURONIC ACID BINDING PEPTIDE AND A β-LACTAM ANTIBIOTIC

(71) Applicant: Emergent BioSolutions Canada Inc., Winnipeg (CA)

(72) Inventors: Laura Saward, Winnipeg (CA); Xiaobing Han, Winnipeg (CA); George G. Zhanel, Winnipeg (CA)

(73) Assignee: EMERGENT BIOSOLUTIONS CANADA INC., Winnipeg (CA)

( * ) Notice: Subject to any disclaimer, the term of this patent is extended or adjusted under 35 U.S.C. 154(b) by 0 days.

(21) Appl. No.: 14/398,402

(22) PCT Filed: May 3, 2013

(86) PCT No.: PCT/CA2013/050346
§ 371 (c)(1),
(2) Date: Oct. 31, 2014

(87) PCT Pub. No.: WO2013/163766
PCT Pub. Date: Nov. 7, 2013

(65) Prior Publication Data
US 2015/0218235 A1 Aug. 6, 2015

Related U.S. Application Data

(60) Provisional application No. 61/642,721, filed on May 4, 2012.

(51) Int. Cl.
| | | |
|---|---|---|
| *A01N 37/18* | (2006.01) | |
| *A61K 38/04* | (2006.01) | |
| *C07K 14/47* | (2006.01) | |
| *A61K 38/14* | (2006.01) | |
| *A61K 31/545* | (2006.01) | |
| *A61K 45/06* | (2006.01) | |
| *A61K 31/407* | (2006.01) | |
| *A61K 31/43* | (2006.01) | |
| *A61K 31/431* | (2006.01) | |
| *A61K 31/496* | (2006.01) | |
| *A61K 31/546* | (2006.01) | |
| *A61K 38/17* | (2006.01) | |

(52) U.S. Cl.
CPC ............ *C07K 14/47* (2013.01); *A61K 31/407* (2013.01); *A61K 31/43* (2013.01); *A61K 31/431* (2013.01); *A61K 31/496* (2013.01); *A61K 31/545* (2013.01); *A61K 31/546* (2013.01); *A61K 38/14* (2013.01); *A61K 38/1709* (2013.01); *A61K 45/06* (2013.01)

(58) Field of Classification Search
CPC .. A61K 2300/00; A61K 31/407; A61K 31/43; A61K 31/431; A61K 31/496; A61K 31/545; A61K 31/546; A61K 38/14; A61K 38/1709; A61K 45/06; C07K 14/47
See application file for complete search history.

(56) References Cited

U.S. PATENT DOCUMENTS 6,271,344 B1 * 8/2001 Turley .................. C07K 14/47
530/326
8,044,022 B2 10/2011 Kolodka et al.

FOREIGN PATENT DOCUMENTS

| WO | 2006130974 A1 | 12/2006 |
| WO | WO2006130974 A1 | 12/2006 |
| WO | 2010091294 A2 | 8/2010 |
| WO | WO2010091294 A2 | 8/2010 |

OTHER PUBLICATIONS

Valand et al. MRSA Infection. British Dental Journal, 2009, vol. 207, No. 7, p. 304.*
Betts et al. Amino Acid Properties and Consequences of Substitutions. Chapter 14. Bioinformatics for Geneticists, 2003. pp. 289-316.*
International Preliminary Report on Patentability, PCT appl. No. PCT/CA2013/050346, 8 pages (Nov. 4, 2014).
Written Opinion of the International Searching Authority, PCT appl. No. PCT/CA2013/050346, 7 pages (Aug. 12, 2013).
Lee, J.C. et al., Modulation of the local neutrophil response by a novel hyaluronic acid-binding peptide reduces bacterial burden during Staphylococcal wound infection. Infection and Immunity, 2010, 78(10): 4176-4186, ISSN 1098-5522. See whole document, especially Abstract, Figure 4C, first and last paragraph of discussion.
Zaleski, K.J., et al., Hyaluronic acid binding peptides prevent experimental staphylococcal wound infection. Antimicrob Agents Chemother., 2006, 50(11): 3856-3860, ISSN 0066-4804. See whole document, especially abstract, Figure 5 and p. 3860.
PCT/CA2013/050346, filed May 3, 2013, International Publication with ISR PCT/CA2013/050346, filed May 3, 2013.
Bonapace et al. Diagnostic Microbiology and Infectious Diseases 2000;38:43-50.
Bonapace et al. Diagnostic Microbiology and Infectious Diseases 2002;44:363-366.

* cited by examiner

*Primary Examiner* — Marcela M Cordero Garcia
(74) *Attorney, Agent, or Firm* — Thompson Coburn LLP

(57) ABSTRACT

Compositions and methods for the treatment of antibiotic resistant *Staphylococcus aureus* infections are provided comprising β-lactam antibiotics, as well as a hyaluronic acid binding peptide. The antibiotics include cephalosporins as well as the ηοη-β lactam antibiotic vancomycin. The methods provide administering the composition to the subject in an amount effective to reduce or eliminate the infection.

29 Claims, No Drawings

SEQUENCE LISTING

<160> NUMBER OF SEQ IDS NOS: 7

<210> SEQ ID NO 1
<211> LENGTH: 27
<212> TYPE: PRT
<213> ORGANISM: Mus sp.

<400> SEQUENCE: 1

Leu Lys Gln Lys Ile Lys His Val Val Lys Leu Lys Val Val Val Lys
1               5                   10                  15

Leu Arg Ser Gln Leu Val Lys Arg Lys Gln Asn
            20                  25

<210> SEQ ID NO 2
<211> LENGTH: 27
<212> TYPE: PRT
<213> ORGANISM: Homo sapiens

<400> SEQUENCE: 2

Leu Lys Gln Lys Ile Lys His Val Val Lys Leu Lys Val Val Val Lys
1               5                   10                  15

Leu Arg Cys Gln Leu Ala Lys Lys Lys Gln Ser
            20                  25

<210> SEQ ID NO 3
<211> LENGTH: 27
<212> TYPE: PRT
<213> ORGANISM: Artificial Sequence
<220> FEATURE:
<223> OTHER INFORMATION: hybPEP35-1 conservative substitution human
      peptide variant

<400> SEQUENCE: 3

Leu Lys Gln Lys Ile Lys His Val Val Lys Leu Lys Val Val Val Lys
1               5                   10                  15

Leu Arg Ser Gln Leu Ala Lys Lys Lys Gln Ser
            20                  25

<210> SEQ ID NO 4
<211> LENGTH: 27
<212> TYPE: PRT
<213> ORGANISM: Artificial Sequence
<220> FEATURE:
<223> OTHER INFORMATION: Reordered human peptide sequence

<400> SEQUENCE: 4

Lys Lys Lys Lys Lys Leu Gln Leu Gln Leu Asn Leu Ile Lys Lys Lys
1               5                   10                  15

Val Gln Val Ser Val Val Val Val Arg Arg His
            20                  25

<210> SEQ ID NO 5
<211> LENGTH: 16
<212> TYPE: PRT
<213> ORGANISM: Artificial Sequence
<220> FEATURE:
<223> OTHER INFORMATION: Laboratory designed HA inhibitor peptide

<400> SEQUENCE: 5

Gly Ala His Trp Gln Phe Asn Ala Leu Thr Val Arg Gly Gly Gly Ser
1               5                   10                  15

-continued

```
<210> SEQ ID NO 6
<211> LENGTH: 12
<212> TYPE: PRT
<213> ORGANISM: Artificial Sequence
<220> FEATURE:
<223> OTHER INFORMATION: Phage display developed HA binding peptide

<400> SEQUENCE: 6

Gly Ala His Trp Gln Phe Asn Ala Leu Thr Val Arg
1               5                   10

<210> SEQ ID NO 7
<211> LENGTH: 4
<212> TYPE: PRT
<213> ORGANISM: Artificial Sequence
<220> FEATURE:
<223> OTHER INFORMATION: Artificial spacer sequence

<400> SEQUENCE: 7

Gly Gly Gly Ser
1
```

ANTIMICROBIAL COMPOSITIONS COMPRISING A HYALURONIC ACID BINDING PEPTIDE AND A β-LACTAM ANTIBIOTIC

CROSS-REFERENCE TO RELATED APPLICATIONS

This application is a U.S. national stage of International Application No. PCT/CA2013/050346, filed May 3, 2013, which claims the benefit of and priority to U.S. Provisional Application no. 61/642,721, filed on May 4, 2012 under the title ANTIMICROBIAL COMPOSITIONS. The content of each of the above patent applications is hereby expressly incorporated by reference into the detailed description hereof.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: EMER_049_01US_SubSeqList.txt, date recorded: Mar. 27, 2015, file size 3 kilobytes).

FIELD OF THE INVENTION

The invention relates to new compositions which comprise selective antibiotics and a peptide. The invention further relates to a method of potentiating the antimicrobial effectiveness of antibiotics for the treatment of bacterial infections in a vertebrate subject. Methods are provided for administering the composition to the vertebrate subject in an amount effective to reduce or eliminate infection or further limit opportunities for antibiotic resistant phenotypes. Methods for the treatment or prevention of *Staphylococcus aureus* infection in an organism are provided.

BACKGROUND OF THE INVENTION

*Staphylococcus aureus* (*S. aureus*) is a ubiquitous gram positive bacterium that can colonize the nares and skin of humans without causing disease. Approximately one third of the human population is colonized with *S. aureus* making it difficult to avoid transmittance. The bacteria can cause a wide variety of disease from mild skin infections to more serious diseases such as bacteremia and endocarditis. The patient populations most at risk are dialysis patients, patients with ventriculoperitoneal shunts, patients at risk of infective endocarditis, patients who are immunocompromised, and residents of nursing homes. In healthcare settings it is the main pathogen responsible for infections of the skin and soft tissues, as well as for those associated with medical procedures and indwelling devices such as catheters. Since catheter- and device-related infections remain the most significant cause of morbidity, prolonged length of stay and increased cost in affected patients, *S. aureus* infections are of concern. *S. aureus* has developed resistance to multiple antibiotics and has a methicillin-resistant variant (MRSA) which is becoming widespread in the community and nosocomial environments. This is leading to increased incidences of infection in both the hospital and community settings. With reduced treatment options available, alternative approaches are required.

*S. aureus* is an important cause of serious infections in both hospitals and community. Unfortunately, this pathogen has the ability to quickly respond to each new antibiotic and has been particularly efficient at developing resistance mechanisms. In 1942, two years after the introduction of penicillin for medical use, the first penicillin-resistant *S. aureus* isolate was observed in a hospital. Since 1960, around 80% of all *S. aureus* strains are resistant to penicillin. In 1961, two years after the introduction of methicillin, a penicillinase-resistant penicillin, *S. aureus*, developed methicillin-resistance due to the acquisition of the mecA gene. During the last several decades, various methicillin-resistant *S. aureus* (MRSA) clones disseminated worldwide become a global health threat and a significant challenge for healthcare systems. Since the widespread emergency of MRSA, vancomycin has represented the cornerstone of therapy for MRSA infections. Over the last decade, strains that are not susceptible to vancomycin have occurred, showing either intermediate resistance (VISA) or, worse, full resistance to this antibiotic (VRSA).

Currently, the rapid emergence of bacteria resistant to commonly used antibiotics has become a serious problem and one of the major challenges for the healthcare systems worldwide. Antibiotic resistant infections are associated with higher treatment cost, longer hospital stay and a 1.3 to 2-fold increase in mortality. The resistant bacteria also spread to community and become broader infection-control problems, since some community-associated resistant strains are more virulent due to the production of virulent factors like toxins.

Despite the urgent need for effective agents to overcome the bacterial resistance, the antibiotic drug discovery and development has slowed considerably in recent years. Traditional approaches and the newer genomic mining approaches have not yielded novel classes of antibacterial compounds. An alternative strategy is to improve analogues of existing classes of antibacterial drugs by modifying the action sites or combining with other compounds to improve the potency and minimize the resistance.

Methicillin resistant bacteria typically exhibit resistance to all, or at least most, β-lactam antibiotics, including penicillins, cephalosporins and carbapenems. β-lactam antibiotics target the transpeptidase activity of penicillin-binding proteins (PBPs) involved in cell wall biosynthesis. The peptidoglycan layer in the bacterial cell wall is a crystallattice structure formed from linear chains of two alternating amino sugars, N-acetylglucosamine (GlcNAc) and N-acetylmuramic acid (MurNAc). Each MurNac is attached to a short amino acid chain, containing L-alanine, D-glutamic acid, L-lysine, and D-alanyl-D-alanine in the case of *S. aureus*. Cross-linking between amino acids in different linear amino sugar occurs with the help of the enzyme transpeptidases and results in a 3-dimensional structure that is strong and rigid. β-lactams contain the highly reactive CO—N bond in the β-lactam ring, which lie in exactly the same position as the CO—N bond in D-alanyl-D-alanine, resulting in nearly identical conformation of the terminal portion of the peptidoglycan peptide chain, which is the target of transpeptidation. The binding of β-lactams to transpeptidase enzymes (also known as penicillin-binding proteins, PBPs) results in acylation of a serine residue in the active site of PBP, this irreversible reaction inactivates the enzyme and prevents the final cross linking (transpeptidation) of the nascent peptidoglycan layer, disrupting cell wall synthesis.

Methicillin sensitive *S. aureus* (MSSA) express four naïve penicillin-binding enzymes (PBP1, PBP2, PBP3, and PBP4), and their activities are specifically prevented by the covalent binding of β-lactam antibiotics to their active sites.

The MRSA isolates acquired the mecA gene, coding for a novel 78 KDa penicillin-binding protein 2a (PBP2a). The crystal structure of PBP2a reveals it to have a closed active site, and the interactions of PBP2a with peptidoglycan at an allosteric site trigger a conformational change that leads to accessibility to the active site. PBP2a is not inhibited in the presence of β-lactams due to the blockage of access to the active site, and is able to take over the peptidoglycan biosynthesis from the naïve PBPs to perform the critical cell wall cross-linking reaction.

Vancomycin is a glycopeptide antibiotic that is able to form hydrogen bond interactions with the terminal D-alanyl-D-alanine moieties of the peptidoglycan (murein) monomer. The binding of vancomycin to the D-Ala-D-Ala prevents cell wall synthesis in two ways. It can completely or partially inhibit the peptidoglycan polymerization if it binds to murein monomers located in the cytoplasmic membrane. It also can target the D-Ala-D-Ala residues in the completed peptidoglycan layers or on the nascent peptidoglycan chain to prevent the cross-linking of the backbone polymers.

VISA and VRSA have emerged almost exclusively from MRSA, with few exceptions involving strains with heteroresistance. Vancomycin resistance does not develop stepwise and VRSA does not progress from VISA, since VISA and VRSA have completely different resistance mechanisms.

The intermediate resistance in VISA has been associated to the presence of a thickened cell wall. The wall is rich in peptidoglycan chains that are not cross-linked and display free terminal D-Ala-D-Ala residues, which act as decoy targets, blocking vancomycin in the external layer of the cell wall and diverting the antibiotic from reaching its true target-peptidoglycan precursors at cytoplasmic membrane level. The cell wall is clogged by the trapped vancomycin and this further block the antibiotic penetration. No characteristic genetic trait has been tightly associated with VISA resistance.

Different from VISA, VRSA strains have acquired the complete genetic apparatus for glycopeptides resistance from vancomycin-resistant enterococci (VRE). VRSA strains acquired the vanA operon that confers high level resistance to glycopeptides, vancomycin and teicoplanin. The vanA operon contains an assembly of genes that encode the synthesis of modified peptidoglycan precursors containing a terminal D-Ala-D-Lac instead of D-Ala-D-Ala and the elimination of the susceptible wild-type targets. The D-alanyl-D-lactate variation results in the loss of one hydrogen-bonding interaction (4, as opposed to 5 for D-alanyl-D-alanine) possible between vancomycin and the peptide, which results in a 1000-fold decrease in affinity. The resistance mechanism is under the regulation of a two-component signal transduction system (gene vanS and vanR), which activates only in the presence of vancomycin.

Therefore, there is an unmet need for effective treatment and/or prevention of S. aureus associated infections that are resistance to current antibiotics, including MRSA, VISA, and VRSA.

SUMMARY OF THE INVENTION

The applicant has discovered that the antibiotic effect of certain antibiotics is synergistically potentiated when they are coadministered with hyaluronic acid binding peptides, specifically PEP35.

According to one aspect of the invention is provided a method for the prevention or treatment of antibiotic resistant S. Aureus infection or reinfection, comprising administering a therapeutically effective amount of a beta-lactam antibiotic and a hyaluronic acid binding peptide.

According to a further aspect of the present invention is the use of a hyaluronic acid binding peptide in the potentiation of a beta-lactam antibiotic against antibiotic resistant S. Aureus.

According to yet a further aspect of the present invention is the use of a hyaluronic acid binding peptide and a beta-lactam antibiotic for the treatment or prevention of antibiotic resistant S. Aureus infection or reinfection.

According to yet a further aspect of the present invention is provided a composition comprising a beta-lactam antibiotic and a hyaluronic acid binding peptide.

In certain embodiments, the S. aureus is a methicillin resistant variant (MRSA), a vancomycin resistant variant (VRSA), or a vancomycin intermediate resistant variant (VISA).

In certain embodiments, the beta-lactam antibiotic and the hyaluronic acid binding peptide are administered simultaneously.

In certain embodiments, the beta-lactam antibiotic and the hyaluronic acid binding peptide are administered concurrently.

In certain embodiments, the beta-lactam antibiotic and the hyaluronic acid binding peptide are administered separately, for example, within 15 minutes of each other.

In certain embodiments, the beta-lactam antibiotic is a cephalosporin.

In certain embodiments, the cephalosporin is a first generation cephalosporin, for example, cefacetrile, Cefadroxil, Cephalexin, Cefaloglycin, Cefalonium, Cefaloridine, Cefalotin, Cefapirin, Cefatrizine, Cefazaflur, Cefazedone, Cefazolin, Cefradine, Cefroxadine, or Ceftezole.

In certain embodiments, the cephalosporin is a second generation cephalosporin, for example, Cefaclor, Cefonicid, Cefprozil, Cefuroxime, Cefuzonam, Cefmetazole, Cefotetan, Cefoxitin Carbacephems or Cephamycins.

In certain embodiments, the cephalosporin is a third generation cephalosporin, for example, Cefcapene, Cefdaloxime, Cefdinir, Cefditoren, Cefetamet, Cefixime, Cefmenoxime, Cefodizime, Cefotaxime, Cefovecin, Cefpimizole, Cefpodoxime, Cefteram, Ceftibuten, Ceftiofur, Ceftiolene, Ceftizoxime, Ceftriaxone, Cefoperazone, Ceftazidime, or Oxacephems.

In certain embodiments, the cephalosporin is a fourth generation cephalosporin, for example, Cefclidine, Cefepime, Cefluprenam, Cefoselis, Cefozopran, Cefpirome, Cefquinome, or Oxacephems.

In certain embodiments, the cephalosporin is a fifth generation cephalosporin, for example, Ceftobiprole, medocaril, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftaroline, Ceftioxide, or Cefuracetime.

In certain embodiments, the antibiotic is selected from methicillin, cefazolin, ceftriaxone, vancomycin, meropenem, and piperacillin/tazobactam.

In certain embodiments, the antibiotic is vancomycin.

In certain embodiments, the hyaluronic acid binding peptide is a PEP35 peptide, for example, a mouse PEP35 having an amino acid sequence represented by SEQ ID NO.: 1, or a human PEP35 having an amino acid sequence represented by SEQ ID NO.: 2, or a hybrid PEP35 having an amino acid sequence represented by SEQ ID NO.: 3, or a scrambled PEP35 having an amino acid sequence represented by SEQ ID NO.: 4.

BRIEF DESCRIPTION OF THE DRAWINGS

NONE

DETAILED DESCRIPTION OF THE INVENTION

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference. As used in this specification and the appended claims, the singular forms "a", "an" and "the" include plural references unless the content clearly dictates otherwise.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Vertebrate," "mammal," "subject," "mammalian subject," or "patient" are used interchangeably and refer to all vertebrates, e.g., mammals and non-mammals, such as mice, sheep, dogs, cows, avian species, ducks, geese, pigs, chickens, amphibians, and reptiles, for example, mammals such as human patients and non-human primates, as well as experimental animals such as rabbits, rats, and mice, cows, horses, goats, dogs, and primates.

The present invention generally relates to compositions and methods for the prevention or treatment of bacterial infection by S. aureus, in a vertebrate. Methods for inducing an immune response to S. aureus infection are provided. The methods provide administering an antibody or agent to subject in need thereof in an amount effective to reduce, eliminate, or prevent S. aureus bacterial infection or bacterial carriage.

"Bacterial carriage" is the process by which bacteria can thrive in a normal subject without causing the subject to get sick. Bacterial carriage is a very complex interaction of the environment, the host and the pathogen. Various factors dictate asymptomatic carriage versus disease. Therefore an aspect of the invention includes treating or preventing bacterial carriage.

"Treating" or "treatment" refers to either (i) the prevention of infection or reinfection, e.g., prophylaxis, or (ii) the reduction or elimination of symptoms of the disease of interest, e.g., therapy. "Treating" or "treatment" can refer to the administration of a composition comprising a polypeptide of interest, e.g., S. aureus alpha-hemolysin antigens or antibodies raised against these antigens. Treating a subject with the composition can prevent or reduce the risk of infection and/or induce an immune response to the polypeptide of interest. Treatment can be prophylactic (to prevent or delay the onset of the disease, or to prevent the manifestation of clinical or subclinical symptoms thereof) or therapeutic suppression or alleviation of symptoms after the manifestation of the disease.

"Preventing" or "prevention" refers to prophylactic administration or vaccination with polypeptide or antibody compositions.

"Therapeutically-effective amount" or "an amount effective to reduce or eliminate bacterial infection" or "an effective amount" refers to an amount of polypeptide or antibiotic that is sufficient to prevent S. aureus bacterial infection or to alleviate (e.g., mitigate, decrease, reduce) at least one of the symptoms associated with S. aureus bacterial infection or to induce an immune response to S. aureus alpha-hemolysin protein. It is not necessary that the administration of the composition eliminate the symptoms of S. aureus bacterial infection, as long as the benefits of administration of compound outweigh the detriments. Likewise, the terms "treat" and "treating" in reference to S. aureus bacterial infection, as used herein, are not intended to mean that the subject is necessarily cured of infection or that all clinical signs thereof are eliminated, only that some alleviation or improvement in the condition of the subject is effected by administration of the composition.

The term "amino acid" as used herein includes the twenty alpha-amino acids found in mammalian proteins, including both the L-isomeric and D-isomeric forms. The term also includes alternate amino acid residues, such as hydroxyproline, α-aminoisobutyric acid, sarcosine, citrulline, cysteic acid, t-butylglycine, t-butylalanine, phenylglycine, cyclohexylalanine, β-alanine, 4-aminobutyric acid, and so forth, which can also be included in the peptide sequence in a completely analogous way. The D forms of the encoded amino acids and of alternate amino acids can, of course, also be employed. The manner of determining relative rate constants, of conducting syntheses, and of conducting selection and analysis is entirely analogous to that described below for the naturally-occurring amino acids. Accordingly, the results in terms of the number of rate constants required, the number of representative peptides in the mixture, etc., are also directly applicable to peptides that include as one, or more, or all residues, these nonencoded amino acids.

The following standard one letter and three letter abbreviations for the amino acid residues may be used throughout the specification: A, Ala-alanine; R, Arg-Arginine; N, Asn-Asparagine; D, Asp-Aspartic acid; C, Cys-Cysteine; Q, Gln-Glutamine; E, Glu-Glutamic acid; G, Gly-Glycine; H, His-Histidine; I, Ile-Isoleucine; L, Leu-Leucine; K, Lys-Lysine; M, Met-Methionine; F, Phe-Phenylalanine; P, Pro-Proline; S, Ser-Serine; T, Thr-Threonine; W, Trp-Tryptophan; Y, Tyr-Tyrosine; and V, Val-Valine.

PEP35 is an anti-infective antimicrobial agent, previously disclosed in U.S. Pat. No. 8,044,022. The sequence of PEP35 is based on the two hyaluronic acid binding domains (HABDs) of the murine HA-binding protein RHAMM (receptor hyaluronic acid-mediated motility). RHAMM, a cell surface receptor.

The HABDs of RHAMM contain B[X7]B motifs (where B is a basic amino acid arginine or lysine), which are shared with other hyaladherins such as CD44, and are believed to interact electrostatically with the negatively charged glucuronic acids of hyaluronic acid. PEP35 contains multiple B[X7]B motifs separated by a tri-valine linker.

PEP35 is a peptide comprised of 27 amino acids with a pI~12.1 and molecular weight of ~3240. It contains multiple positive charges at physiological pH, due to the presence of eight lysine residues as well as two arginines and one histidine residue in addition to an unmodified N-terminus. The C-terminal end is amidated to improve peptide half-life. The remaining residues on the peptide chain are hydrophobic resulting in an amphipathic peptide. Based on CD analysis, the peptide is capable of alpha-helix formation in polar environments. The sequence of PEP35 is: LKQKIKHVVKLKVVVKLRSQLVKRKQN (SEQ ID NO.:1).

Several variants of the PEP35 sequence were synthesized and tested. The equivalent peptide structure hPEP35 was based on the human RHAMM domain 1 and 2 linked by a tri-valine sequence. Conservative substitutions to the human peptide variant of PEP35 were also synthesized and tested (hybPEP35-1). Although all of these peptides are very similar in size and charge, surprising differences in efficacy were noted in various assays.

Peptide sequences are found below:

| Peptides | Sequence |
| --- | --- |
| PEP35 | LKQKIKHVVKLKVVVKLRSQLVKRKQN (SEQ ID NO.: 1) |
| hPEP35 | LKQKIKHVVKLKVVVKLRCQLAKKKQS (SEQ ID NO.: 2) |
| hybPEP35-1 | LKQKIKHVVKLKVVVKLRSQLAKKKQS (SEQ ID NO.: 3) |
| Scrambled PEP35 (PEP #5) | KKKKKLQLQLNLIKKKVQVSVVVVRRH (SEQ ID NO.: 4) |
| PEP52 | GAHWQFNALTVRGGGS (SEQ ID NO.: 5) |

The sequence of PEP35 is based on the two hyaluronic acid binding domains (HABDs) of the mouse HA-binding protein RHAMM (receptor hyaluronic acid-mediated motility).

| PEP35 | Sequence | BX7Bs | Mass | pI | Charge |
| --- | --- | --- | --- | --- | --- |
| mouse 10+ | LKQKIKHVVKLKVVV KLRSQLVKRKQN (SEQ ID NO.: 1) | 4 | 3239 | 12.1 | 10+ 0− = |
| human 10+ | LKQKIKHVVKLKVVV KLRCQLAKKKQS (SEQ ID NO.: 2) | 4 | 3172 | 10.9 | 10+ 0− = |
| hybrid 1 10+ | LKQKIKHVVKLKVVV KLRSQLAKKKQS (SEQ ID NO.: 3) | 4 | 3156 | 11.5 | 10+ 0− = |

The scrambled PEP35 (PEP#5, SEQ ID NO.:4) contains the same 27 a.a. as PEP35 (SEQ ID NO.:1) does, but reordered to not contain any BX7B motifs. It does, however, contain other BXB motifs, including: X1, X2, X3, X8 and X9. PEP35 has the potential to form a helix based on CD data. PEP35 has at least 6 uninterrupted hydrophobic residues on the wheel in a face of helix; while scrambled PEP35 has 5 uninterrupted hydrophobic residues in a face. This implies that PEP35 and scrambled PEP35 potentially have some degree of similar activities.

PEP52 (SEQ ID NO.: 5) is a HA inhibitor peptide designed by Mark E. Mummert (J. Exp. Med., vol 192, 2000). A 12-mer peptide (GAHWQFNALTVR (SEQ ID NO.: 6)) was developed by using phage display technology, and showed specific binding to soluble, immobilized, and cell-associated forms of HA. Mummert designed the synthetic peptide to include the spacer sequence G-G-G-S(SEQ ID NO.: 7) at the COOH terminus to mimic the original configuration of the peptide moieties fused to the pIII proteins and displayed on phage surfaces.

Cephalosporins are a class of β-lactam antibiotics originally derived from the fungi *Acremonium*, and are generally known in the art. They are structurally and pharmacologically related to the penicillins. Like the penicillins, cephalosporins have a beta-lactam ring structure that interferes with synthesis of the bacterial cell wall and so are bactericidal.

The cephalosporin nucleus can be modified to gain different properties. Cephalosporins are sometimes grouped into "generations" by their antimicrobial properties. The first cephalosporins were designated first generation, whereas later, more extended spectrum cephalosporins were classified as second-generation cephalosporins. Each newer generation of cephalosporins has significantly greater Gram-negative antimicrobial properties than the preceding generation, in most cases with decreased activity against Gram-positive organisms. Fourth-generation cephalosporins, however, have true broad spectrum activity.

Although first-generation cephalosporins are moderate spectrum agents, with a spectrum of activity of bacteria that includes penicillinase-producing, methicillin-susceptible staphylococci and streptococci, they are not the drugs of choice for such infections. They also have activity against some *Escherichia coli*, *Klebsiella pneumoniae* and *Proteus mirabilis*, but have no activity against *Bacteroides fragilis*, enterococci, methicillin-resistant staphylococci, *Pseudomonas, Acinetobacter, Enterobacter*, indole-positive *Proteus*, or *Serratia*. First-generation cephalosporins include; Cefacetrile (cephacetrile), Cefadroxil (cefadroxyl; Duricef), Cephalexin (cephalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole.

The second-generation cephalosporins have a greater Gram-negative spectrum while retaining some activity against Gram-positive cocci. They are also more resistant to beta-lactamase. Second-generation cephalosporins include Cefaclor (Ceclor, Distaclor, Keflor, Raniclor), Cefonicid (Monocid), Cefprozil (cefproxil; Cefzil), Cefuroxime (Zinnat, Zinacef, Ceftin, Biofuroksym), Cefuzonam, Cefmetazole, Cefotetan, Cefoxitin Carbacephems (loracarbef, Lorabid) and Cephamycins.

Third-generation cephalosporins have a broad spectrum of activity and further increased activity against Gram-negative organisms. Some members of this group (in particular, those available in an oral formulation, and those with anti-pseudomonal activity) have decreased activity against Gram-positive organisms. Third-generation cephalosporins include Cefcapene, Cefdaloxime, Cefdinir (Omnicef, Kefnir), Cefditoren, Cefetamet, Cefixime (Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Fortum, Fortaz), Oxacephems (latamoxef, moxalactam).

Fourth-generation cephalosporins are extended-spectrum agents with similar activity against Gram-positive organisms as first-generation cephalosporins. They also have a greater resistance to beta-lactamases than the third-generation cephalosporins. Fourth-generation cephalosporins include Cefclidine, Cefepime (Maxipime), Cefluprenam, Cefoselis, Cefozopran, Cefpirome (Cefrom), Cefquinome, Oxacephems (flomoxef).

Cephalosporins that are described as "fifth generation" or yet to be classified include Ceftobiprole (and the soluble prodrug medocaril), Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftaroline, Ceftioxide, Cefuracetime.

EXAMPLES

Example 1

Minimum MIC of Four Peptides

Activity of the four peptides PEP35, scrambled PEP35, hybPEP35-1 and PEP-52 (SEQ ID NOs.: 1, 4, 3, and 5, respectively) were assessed against MRSA (both community-acquired, eg. USA400/CMRSA10, and healthcare-acquired eg USA100/800), obtained from the CANWARD study [(Canadian Journal of Infectious Diseases and Medical Microbiology 2009; 20 (Suppl A): 3-71)]. VISA (strains 92, 95 and 96), VRSA (strains 105 and 106) and $E.$ $coli$ (strain 69717) isolates were also tested. One MSSA was used as a control. All MICs were assessed using CLSI guidelines. Also assessed was the activity of cefazolin, ceftriazone, meropenem, and a piperacillin/tazobactam combination antibiotic. Minimum inhibitory concentration (MIC) is the lowest concentration of an antimicrobial that will inhibit the visible growth of a microorganism after incubation.

Antimicrobial Susceptibility Testing: A custom designed panel of antimicrobials was created. The panel included: PEP35, penicillin, piperacillin/tazobactam, cefazolin, ceftriaxone, meropenem, clarithromycin, clindamycin, gentamicin, amikacin, vancomycin, ciprofloxacin, levofloxacin, moxifloxacin, linezolid, trimethoprim/sulfamethoxazole and doxycycline. These agents were obtained as laboratory grade powders from their respective manufacturers. Stock solutions were prepared and dilutions made as described by the Clinical Laboratory Standards Institute (2005 CLSI). Following two subcultures from frozen stock the MICs of the antimicrobial agents for the isolates were determined by the CLSI 2005 approved broth macrodilution method. Briefly, test tubes containing doubling antibiotic dilutions (2 ml per tube) of cation adjusted Mueller-Hinton broth (eg. for Enterobacteriaceae) with or without lysed horse blood (2-5% V/V) [eg. for $S.$ $pneumoniae$] were inoculated to achieve a final concentration of approximately $5 \times 10^5$ CFU/ml and incubated in ambient air for 24 hours prior to reading. Colony counts were performed periodically to confirm inocula. Quality control was performed every two weeks using a variety of ATCC QC organisms including; $S.$ $aureus$ 29213, $E.$ $faecalis$ 29212, $E.$ $coli$ 25922 and $P.$ $aeruginosa$ 27853. For all antimicrobials as well as PEP35, CLSI criteria were used. PEP35 was solubilized in 10 mM sodium acetate. Results were tabulated in Table 1. PEP35 and scrambled PEP35 exhibited similar activity, versus MRSA, VISA and VRSA and $E.$ $coli$. HybPEP35-1 and PEP52 exhibited no activity versus MRSA, VISA, VRSA and $E.$ $coli$.

Example 2

Checkerboard Assays

Checkerboard assays were carried out as described by Bonapace et al.

Diagnostic Microbiology and Infectious Diseases 2002; 44:363-366. In brief, checkerboard assays were performed in 96 well microtitre trays using an 8-by-8 well configuration. Dilutions of each antimicrobial were performed with concentrations ranging from 0.03×MIC to 4×MIC. 96-well custom designed microtitre plates contained 100 ul/well of cation adjusted Mueller-Hinton broth (eg. for Enterobacteriaceae) with or without lysed horse blood (2-5% V/V) [eg. for $S.$ $pneumoniae$] and were inoculated to achieve a final concentration of approximately $5 \times 10^5$ CFU/ml and incubated in ambient air for 24 hours prior to reading. Colony counts were performed periodically to confirm inocula. Quality control was performed every two weeks using a variety of ATCC QC organisms including; $S.$ $pneumoniae$ 49619, $S.$ $aureus$ 29213, $E.$ $faecalis$ 29212, $E.$ $coli$ 25922 and $P.$ $aeruginosa$ 27853. The checkerboard assays were carried out with four peptides (PEP35, scrambled PEP35, Hyb-PEP35-1 and PEP-52) versus MRSA, VISA, VRSA and $E.$ $coli$ with MSSA (as a control). All peptides were assessed for synergy with β-lactams and vancomycin. For all antimicrobials as well as the peptides, CLSI criteria were used.

The fractional inhibitory concentration index (FIC index) was used to interpret synergy, antagonism or additivity/indifference. FIC index=FIC of drug A+FIC of drug B where:

The FIC of drug A and drug B was calculated as follows, FIC drug A=MIC of drug A in combination/MIC of drug A alone and FIC of drug B=MIC of drug B in combination/MIC of drug B alone. Synergy was defined as FIC index ≤0.5, additivity/indifference defined as a FIC between 0.5 and 4 and antagonism defined as an FIC index >4. Results were tabulated in Tables 2-4. This data suggests that both PEP35 and scrambled PEP35 showed synergistic effect with cefazolin and ceftriaxone, versus CA-MRSA, HA-MRSA, VISA and VRSA, and with meropenem versus CA-MRSA, HA-MRSA, and VISA. The data also suggest that PEP35 and scrambled PEP35 were not synergistic with β-lactams (except at a very low level, with ceftriaxone), against $E.$ $Coli$. Finally, the data suggest that Pep52 exhibited no synergistic activity.

Example 3

MICs of PEP35 with Cephalosporins

Cefazolin, ceftriaxone and vancomycin MICs were performed against MRSA (both community-acquired, eg. USA300/CMRSA10, and healthcare-acquired), VISA (strains 92, 95 and 96) and VRSA (strains 105 and 106) isolates using fixed concentrations of PEP35 (8 ug/ml and 32 ug/ml). One MSSA was used as a control. All MICs were assessed using CLSI guidelines.

Example 4

Checkerboard Assay—Timing

The checkerboard assays were carried out with PEP35 and cefazolin, ceftriaxone or vancomycin versus 2 isolates of MRSA using the methods previously described in example 2. In these checkerboard studies, PEP35 and the cephalosporins were added 15 minutes before the other to determine if pre-exposure to the peptide or antibiotic is required for the synergy. Thus, experiments were performed to expose the MRSA to PEP35, 15 minutes before the addition of the cephalosporin or vancomycin, as well as the opposite (to expose the MRSA to cephalosporins 15 minutes before exposure to PEP35).

The fractional inhibitory concentration index (FIC index) was used to interpret synergy, antagonism or additivity/indifference. FIC index=FIC of drug A+FIC of drug B where the FIC of drug A and drug B was calculated as follows, FIC drug A=MIC of drug A in combination/MIC of drug A alone and FIC of drug B=MIC of drug B in combination/MIC of drug B alone. Synergy was defined as FIC index ≤0.5, additivity/indifference defined as an FIC of between 0.5 and 4 and antagonism defined as an FIC index >4. Results were tabulated in Tables 5-10. Cephalosporin MICs, versus CA-MRSA, HA-MRSA, and VRSA, were reduced in a concentration dependent fashion, in the presence of PEP35. The MIC was not affected by the order in which PEP35 and cephalosporin were added to the assays. The results also showed that PEP35 activity on vancomycin MICs versus VRSA was concentration dependent, but order neutral.

Example 5

Checkerboard Assay—Versus Gram Positive and Gram Negative Bacteria

To assess whether any synergy, antagonism or additivity/indifference occurs when PEP35 is combined with marketed antimicrobials against a variety of Gram-positive and Gram-negative organisms from respiratory, skin/skin structure, urinary and bacteremic pathogens obtained from Canadian hospitalized patients.

The checkerboard assays were carried out as described by Eliopoulos and Moellering (Chapter 9) in Antibiotic in Laboratory Medicine, Lorian Ed. 1996 as well as Bonapace et al. Diagnostic Microbiology and Infectious Diseases 2002; 44:363-366 and Bonapace et al. Diagnostic Microbiology and Infectious Diseases 2000; 38:43-50. In brief, checkerboard assays were performed in 96 well microtitre trays using an 8-by-8 well configuration. Dilutions of each antimicrobial were performed with concentrations ranging from 0.03×MIC to 4×MIC. 96-well custom designed microtitre plates contained 100 ul/well of cation adjusted Mueller-Hinton broth (eg. for Enterobacteriaceae) with or without lysed horse blood (2-5% V/V) [eg. for $S.$ $pneumoniae$] and were inoculated to achieve a final concentration of approximately $5 \times 10^5$ CFU/ml and incubated in ambient air for 24 hours prior to reading. Colony counts were performed periodically to confirm inocula. Quality control was performed every two weeks using a variety of ATCC QC organisms including; $S.$ $pneumoniae$ 49619, $S.$ $aureus$ 29213, $E.$ $faecalis$ 29212, $E.$ $coli$ 25922 and $P.$ $aeruginosa$ 27853. For all antimicrobials as well as PEP35, CLSI criteria was used.

The fractional inhibitory concentration index (FIC index) was used to interpret synergy, antagonism or additivity/indifference. FIC index=FIC of drug A+FIC of drug B where:
The FIC of drug A and drug B is calculated as follows, FIC drug A=MIC of drug A in combination/MIC of drug A alone and FIC of drug B=MIC of drug B in combination/MIC of drug B alone. Synergy is defined as FIC index ≤0.5, additivity/indifference FIC >0.5-4 and antagonism FIC index >4.

Antimicrobials used included PEP35, cefazolin, ceftriaxone, vancomycin, linezolid, tigecycline and daptomycin versus Gram-positive cocci and PEP35, gentamicin, levofloxacin, piperacillin/tazobactam, meropenem and colistin (Polymyxin E) versus Gram-negative bacilli. These agents were obtained as laboratory grade powders from their respective manufacturers. Stock solutions were prepared and dilutions made as described by the Clinical Laboratory Standards Institute (2005 CLSI).

Organisms included Gram-positive cocci (2 strains of each): Methicillin-susceptible $Staphylococcus$ $aureus$ (MSSA), community-associated (CA) and healthcare-associated (HA) methicillin-resistant $Staphylococcus$ $aureus$ (MRSA), vancomycin-intermediate $Staphylococcus$ $aureus$ (VISA), vancomycin-resistant $Staphylococcus$ $aureus$ (VRSA), methicillin-resistant $Staphylococcus$ $epidermidis$ (MRSE), $Streptococcus$ $pyogenes$, $Streptococcus$ $agalactiae$, $Streptococcus$ $pneumoniae$, $Enterococcus$ $faecalis$, $Enterococcus$ $faecium$ and vancomycin-resistant $enterococcus$ (VRE). Gram-negative bacilli tested (2 strains of each) included: $E.$ $coli$, $Pseudomonas$ $aeruginosa$, $Klebsiella$ $pneumoniae$, $K.$ $oxytoca$, $Enterobacter$ $cloacae$, $P.$ $mirabilis$ and $Stenotrophomonas$ $maltophilia$. MIC testing, following two subcultures from frozen stock were determined by the CLSI 2005 approved broth microdilution method.

Example 6

MICs of PEP35 with and without Cefazolin or Cephalexin Against MRSA

Cefazolin and cephalexin MICs were performed against MRSA (50 community-acquired (CA-MRSA) and 50 healthcare-acquired (HA-MRSA) isolates) using a fixed concentration of PEP35 (32 ug/ml). One MS SA and ATCC reference strains were used as controls. All MICs were assessed using CLSI guidelines.

Results

Table 1 shows the activity of Cangene peptides versus MRSA, VISA, VRSA and $E.$ $coli$. These data show that PEP35 and scrambled PEP35 demonstrate similar activity versus MRSA, VISA and VRSA. Unlike PEP35, scrambled PEP35 was active vs $E.$ $coli$. Other Cangene peptides (HybPEP35-1 or PEP52) were not active versus these organisms.

Table 2 shows the synergy studies with β-lactams and PEP35 versus MRSA, VISA, VRSA and $E.$ $coli$. These data show that PEP35 is synergistic with cefazolin, ceftriaxone and meropenem versus CA-MRSA, HA-MRSA, VISA and VRSA (not meropenem). No combination of PEP35 and β-lactams were synergistic versus $E.$ $coli$.

Table 3 describes synergy studies with β-lactams and Scrambled PEP35 versus MRSA, VISA, VRSA and $E.$ $coli$. These data show that like PEP35, scrambled PEP35 is synergistic with cefazolin, ceftriaxone and meropenem versus CA-MRSA, HA-MRSA, VISA and VRSA (not meropenem). The combination of scrambled PEP35 and β-lactams were not synergistic (except at low level with ceftriaxone) versus $E.$ $coli$.

Table 4 shows the synergy studies with β-lactams and PEP-52 versus MRSA, VISA, VRSA and $E.$ $coli$. These data show no synergistic activity with PEP_52 and β-lactams.

Table 4b shows the synergy studies with β-lactams and HybPEP35-1 Versus MRSA, VISA, VRSA and $E.$ $coli$. The data shows synergistic activity with HybPEP35-1 and certain β-lactams, against certain isolates.

Table 5 shows the effect of increasing the concentrations of PEP35 on cephalosporin activity (MICs) versus CA-MRSA and HA-MRSA. These data show that cephalosporin MICs versus CA-MRSA and HA-MRSA are reduced in the presence of PEP35 and that these cephalosporin MICs are reduced in a concentration dependent fashion.

Table 5 also shows the effect of adding PEP35 15 minutes before or after cephalosporins on activity (MICs) versus CA-MRSA and HA-MRSA. These data show that whether PEP35 is added 15 minutes before the cephalosporin or the cephalosporin is added 15 minutes before PEP35 does not in any way influence the MIC.

Table 6 shows the effect of increasing the concentrations of PEP35 on cephalosporin activity (MICs) versus CA- MRSA, HA-MRSA, VISA and VRSA. These data show that cephalosporin MICs versus CA-MRSA, HA-MRSA and VRSA are reduced in the presence of PEP35 and that these cephalosporin MICs are reduced in a concentration dependent fashion. PEP35 reduced the MICs of cephalosporins versus VISA in 2 of 3 strains and this reduction was concentration dependent. Values from independent experiments for each condition shown in table separated by a "/".

Table 7 shows the effect of adding PEP35 15 Minutes before or after cephalosporins on synergy versus CA-MRSA and HA-MRSA. These data show that whether PEP35 is added 15 minutes before the cephalosporin or the cephalosporin is added 15 minutes before PEP35, does not in any way influence the presence of synergy. Synergy occurs with PEP35 and cephalosporins versus CA-MRSA and HA-MRSA.

Table 8 shows the effect of increasing the concentration of PEP35 on vancomycin activity (MICs) versus VRSA. These data show that PEP35 activity on vancomycin MIC is concentration dependent. Increasing the concentration of PEP35 lowers the vancomycin MIC. Table 8 also shows the effect of adding PEP35 15 Minutes before or after vancomycin on activity (MICs) versus VRSA. These data show that whether PEP35 is added 15 minutes before the vancomycin or the vancomycin is added 15 minutes before PEP35, does not in any way influence the vancomycin MIC.

Table 9 shows the effect of adding PEP35 15 minutes before or after vancomycin on synergy versus VRSA. These data show that whether PEP35 is added 15 minutes before the vancomycin or the vancomycin is added 15 minutes before PEP35, does not in any way influence synergy. PEP35 and vancomycin are synergistic versus VRSA.

Table 10 shows the effect of increasing PEP35 concentration on activity (MICs) with and without vancomycin versus MRSA, VISA and VRSA. These data show that PEP35 activity on vancomycin MIC is concentration dependent for VRSA and that VRSA MICs decrease significantly with PEP35. No effect on MIC occurred with PEP35 and vancomycin versus MRSA or VISA. Values from independent experiments for each condition shown in table separated by a "/".

Table 11 shows the synergy studies with PEP35 versus Gram-positive cocci, in combination with cefazolin, ceftriaxone, daptomycin, linezolid, tigecycline and vancomycin did not demonstrate antagonism against any streptococci, staphylococci and enterococci tested. Versus Gram-positive cocci, PEP35 interacted with cefazolin, ceftriaxone, daptomycin, linezolid, tigecycline and vancomycin in an additive fashion against all streptococci, staphylococci and enterococci tested with the exception of CA-MRSA and HA-MRSA. Versus CA-MRSA and HA-MRSA, PEP35 (MIC alone, range 512-1024 ug/ml) with both beta-lactams tested (cefazolin and ceftriaxone, [MIC alone, range 16-256 ug/ml]) interacted in a synergistic fashion (FIC index≤0.5).

Table 12 shows the synergy studies with PEP35 Versus Gram-negative bacilli, in combination with gentamicin, levofloxacin, piperacillin-tazobactam, meropenem, and colistin (polymyxin E). PEP35 did not demonstrate antagonism or synergy against any Gram-negative bacilli tested. Versus Gram-negative bacilli, PEP35 in combination with gentamicin, levofloxacin, piperacillin-tazobactam, meropenem, and colistin (polymyxin E) interacted in an additive fashion with all Gram-negative bacilli tested.

Table 13 shows the synergy studies with HybPEP35-1 versus gram positive cocci in combination with cefazolin, ceftriaxone, meropenem and pipercillin-tazobactam. The data shows synergy in certain isolates between HybPEP35-1 and β-lactams and meropenem. Strong synergy was evident versus CA-MRSA, weak synergy was found with one HA-MRSA and stronger synergy with another HA-MRSA strain. Synergy ranged from mild to strong for VISA and VRSA. Values from independent experiments for each condition shown in table separated by a "/".

Table 14 shows the in vitro activity of PEP35 with 50 CA-MRSA strains with and without Cefazolin or Cephalexin. Cefazolin alone MICs ranged from 2-256 ug/ml with 45 of the 50 strains being resistant to cefazolin. Combining PEP35 with cefazolin resulted in MIC reductions of 2-128 fold, with 32-64 fold reductions being most common. All CA-MRSA MICs with combination of PEP35 with cefazolin were ≤4 ug/ml, which is considered susceptible (≤8 ug/ml) as per CLSI breakpoints.

Cephalexin alone MICs ranged from 64-512 ug/ml with 50 of the 50 strains being resistant to cephalexin. Combining PEP35 with cephalexin resulted in MIC reductions of 4-32 fold, with 4-8 fold reductions being the most common. 16% of CA-MRSA MICs with combination of PEP35 with cephalexin were ≤8 ug/ml, which is considered susceptible as per CLSI breakpoints.

Table 15 shows the in vitro activity of PEP35 with 50 HA-MRSA strains with and without Cefazolin or Cephalexin. Cefazolin alone MICs ranged from 2-512 ug/ml with 47 of the 50 strains being resistant to cefazolin. Combining PEP35 with cefazolin resulted in MIC reductions of 0-256 fold, with 4-32 fold reductions being most common. 64% of HA-MRSA MICs with combination of PEP35 with cefazolin were ≤8 ug/ml, which is considered susceptible (≤8 ug/ml) as per CLSI breakpoints.

Cephalexin alone MICs ranged from 128-512 ug/ml with 50 of the 50 strains being resistant to cephalexin. Combining PEP35 with cephalexin resulted in MIC reductions of 0-32 fold, with 2-4 fold reductions being the most common. 4% of HA-MRSA MICs with combination of PEP35 with cephalexin were ≤8 ug/ml, which is considered susceptible as per CLSI breakpoints.

As would be evident to a person of skill in the art, often, when faced with a clinical situation, it is not known which strain is being combated. As such, a combination exhibiting synergy against some strains, and effectiveness (but not necessarily synergy) against others, is, in all cases, a useful and powerful weapon against infection, regardless of whether it offers synergy against the specific strain, since the specific strain is sometimes not known, and the treatment will, in many cases, work better than the alternative treatment.

TABLE 1

| | MIC Activity of Cangene Peptides Versus MRSA, VISA, VRSA and E. coli | | | | | | | |
| --- | --- | --- | --- | --- | --- | --- | --- | --- |
| ISOLATE | Cefazolin | Ceftriaxone | Meropenem | Piperacillin/ Tazobactam | PEP35 | Scrambled PEP35 | HybPEP35-1 | PEP-52 |
| MSSA 79333 | 1 | 8 | 0.12 | ≤1 | 128 | 64 | 256 | >512/?≤128 |
| CA-MRSA 69615 (USA400) | 64 | 256 | 0.5 | 32 | 512 | 256 | >2048/512 | >512/1024 |

TABLE 1-continued

MIC Activity of Cangene Peptides Versus MRSA, VISA, VRSA and E. coli

| | | | | | | | | |
|---|---|---|---|---|---|---|---|---|
| CA-MRSA 70857 (USA400) | 32 | 128 | 2 | 32 | 256 | 256 | >2048/512 | >512/1024 |
| HA-MRSA 77090 (USA100/800) | 128 | 512 | 4 | 16 | 256 | 512 | >2048/512 | >512/1024 |
| HA-MRSA 70798 (USA100/800) | 512 | 2048 | 64 | 4 | 512 | 256 | >2048/1024 | >512/>1024 |
| VRSA 105 | 256 | 2048 | 32 | 64 | 128 | 64 | 256/128 | >512/>1024 |
| VRSA 106 | 256 | 1024 | 16 | 64 | 128 | 128 | 256 | >512/>1024 |
| VISA 92 | 128 | 1024 | 16 | 64 | 1024 | 2048 | >2048/>2048 | >512/1024 |
| VISA 95 | 128 | 512 | 16 | 64 | 1024 | 2048 | >2048/2048 | >512/1024 |
| VISA 96 | 64 | 256 | 8 | 64 | 512 | 1024 | 1024 | >512/1024 |

| ISOLATE | Cefazolin | Ceftriaxone | Meropenem | Piperacillin/ Tazobactam | PEP 35 | Scrambled PEP 35 (28-00639) | hybPEP35-1 (RC-0127) | PEP-52 (28-00900) |
|---|---|---|---|---|---|---|---|---|
| E.coli 69716 | 2 | ≤1 (0.03) | 0.03 | 2 | 128 | 8 | 64 | >512/>1024 |
| E.coli 70752 | 128 | >64 (1024) | 0.03 | 8 | 128 | 8 | 32 | |

TABLE 2

Synergy Studies With β-lactams and PEP35 Versus MRSA, VISA, VRSA and E. coli

| ISOLATE | Cefazolin Avg ΣFIC (range) | Ceftriaxone Avg ΣFIC (range) | Meropenem Avg ΣFIC (range) | Piperacillin/Tazobactam Avg ΣFIC (range) |
|---|---|---|---|---|
| MSSA 79333 | 0.56 (0.37-1.015) | 0.61 (0.37-1.03) | 0.52 (0.37-0.62) | |
| CA-MRSA 69615 (USA400) | 0.24 (0.06-0.53) | 0.30 (0.12-0.56) | 0.49 (0.24-1.008) | |
| HA-MRSA 70798 (USA100/800) | 0.27 (0.09-0.53) | 0.24 (0.075-0.53) | 0.30 (0.12-0.53) | |
| VRSA 106 | 0.39 (0.12-1.015) | 0.26 (0.09-0.53) | 0.91 (0.62-1.12) | |
| VISA 96 | 0.24 (0.06-0.53) | 0.28 (0.09-0.56) | 0.41 (0.24-0.62) | |
| E. coli 69716 | 1.1 (1.0-1.25) | 1.04 (0.56-2.015) | 1.21 (1.03-1.5) | 0.87 (0.56-1.12) |
| E. coli 70752 | | | | 0.98 (0.62-1.25) |

TABLE 3

Synergy Studies With β-lactams and Scrambled PEP35 Versus MRSA, VISA, VRSA and E. coli

| ISOLATE | Cefazolin Avg ΣFIC (range) | Ceftriaxone Avg ΣFIC (range) | Meropenem Avg ΣFIC (range) | Piperacillin/Tazobactam Avg ΣFIC (range) |
|---|---|---|---|---|
| MSSA 79333 | 0.57 (0.50-0.56) | 0.98 (0.62-1.25) | 1.11 (1.0-1.25) | |
| CA-MRSA 69615 (USA400) | 0.24 (0.06-0.53) | 0.31 (0.15-0.56) | 0.70 (0.37-1.03) | |
| HA-MRSA 70798 (USA100/800) | 0.35 (0.018-0.56) | 0.32 (0.015-0.56) | 0.38 (0.31-0.53) | |
| VRSA 106 | 0.52 (0.28-1.06) | 0.39 (0.28-0.56) | 0.91 (0.62-1.12) | |
| VISA 96 | 0.30 (0.12-0.53) | 0.26 (0.09-0.53) | 0.45 (0.31-0.56) | |
| E. coli 69716 | 1.1 (1.0-1.25) | 0.41 (0.26-0.56) | 1.21 (1.03-1.5) | 0.59 (0.37-1.015) |
| E. coli 70752 | | | | 0.67 (0.5-1.06) |

TABLE 4

Synergy Studies With β-lactams and PEP-52 Versus MRSA, VISA, VRSA and E. coli

| ISOLATE | Cefazolin Avg ΣFIC (range) | Ceftriaxone Avg ΣFIC (range) | Meropenem* Avg ΣFIC (range) | Piperacillin/Tazobactam Avg ΣFIC (range) |
|---|---|---|---|---|
| MSSA 79333 | >1* | >1* | >1* | |
| CA-MRSA 69615 (USA400) | >0.5* | >0.5* | >1* | |
| HA-MRSA 70798 (USA100/800) | >1* | >1* | >1* | |
| VRSA 106 | >1* | >1* | >1* | |
| VISA 96 | >1* | >1* | >1* | |
| E. coli 69716 | >1* | >1* | >1* | >1* |
| E. coli 70752 | | | | >1* |

*PEP52 MIC > 1024

TABLE 4b

Synergy Studies With β-lactams and HybPEP35-1 Versus MRSA, VISA, VRSA and E. coli

| ISOLATE | Cefazolin Avg ΣFIC (range) | Ceftriaxone Avg ΣFIC (range) | Meropenem* Avg ΣFIC (range) | Pippercillin/Tazobactam Avg ΣFIC (range) |
|---|---|---|---|---|
| MSSA 79333 | 0.57 (0.50-0.56) | 0.98 (0.62-1.25) | 1.11 (1.0-1.25) | |
| CA-MRSA 69615 (USA400) | 0.24 (0.06-0.53) | 0.31 (0.15-0.56) | 0.70 (0.37-1.03) | |
| HA-MRSA 70798 (USA100/800) | 0.35 (0.018-0.56) | 0.32 (0.015-0.56) | 0.38 (0.31-0.53) | |
| VRSA 106 | 0.52 (0.28-1.06) | 0.39 (0.28-0.56) | 0.91 (0.62-1.12) | |
| VISA 96 | 0.30 (0.12-0.53) | 0.26 (0.09-0.53) | 0.45 (0.31-0.56) | |
| E. coli 69716 | 1.1 (1.0-1.25) | 0.41 (0.26-0.56) | 1.21 (1.03-1.5) | 0.59 (0.37-1.015) |
| E. coli 70752 | | | | 0.67 (0.5-1.06) |

*frozen HybPEP35-1 stock used

TABLE 5

Effect of Increasing Concentration of PEP35 or Adding PEP35 15 Minutes Before or After Cephalosporins on Activity (MICs) Versus CA-MRSA and HA-MRSA

| ORGANISM | PEP35 | CEFAZOLIN | CEFAZOLIN & PEP35 (8 ug/mL) | CEFAZOLIN & PEP35 (32 ug/mL) | CEFTRIAXONE | CEFTRIAXONE & PEP35 (8 ug/mL) | CEFTRIAXONE & PEP35 (32 ug/mL) |
|---|---|---|---|---|---|---|---|
| CA-MRSA 69615 (USA400) | 256 | 64 | 16 | ≤2 | 256 | 64 | 16 |
| CA-MRSA 69615 (USA400)[a] | | 64 | 32 | ≤2 | 512 | 128 | 16 |
| CA-MRSA 69615 (USA400)[b] | | 64 | 32 | ≤2 | 256 | 128 | 16 |
| HA-MRSA 77090 (USA100/800) | 256 | 128 | 4 | ≤2 | 1024 | 64 | 16 |
| HA-MRSA 77090 (USA100/800)[a] | | 128 | 8 | ≤2 | 512 | 64 | 16 |
| HA-MRSA 77090 (USA100/800)[b] | | 128 | 8 | ≤2 | 512 | 64 | 16 |

[a] CFZ or CTR added 15 minutes post PEP35 & organism exposure;
[b] PEP35 added 15 minutes post CFZ or CTR & organism exposure

TABLE 6

Effect of Increasing Concentration of PEP35 on Cephalosporin Activity (MICs) Versus CA-MRSA, HA-MRSA VISA and VRSA

| ISOLATE | PEP35 | CEFAZOLIN | CEFAZOLIN & PEP35 (8 ug/mL) | CEFAZOLIN & PEP35 (32 ug/mL) | CEFTRIAXONE | CEFTRIAXONE & PEP35 (8 ug/mL) | CEFTRIAXONE & PEP35 (32 ug/mL) |
|---|---|---|---|---|---|---|---|
| MSSA 79333 | 256/256/128 | 0.5/0.5 | 0.5/0.5 | 0.5/0.25 | 4/4 | 4/2 | 2/2 |
| CA-MRSA 69615 (USA400) | 512/512/256/512/512 | 64/32/8/32 | 8/≤2/0.5/2 | ≤2/≤2/1/1 | 128/64/256 | 32/16/32 | 16/16/16 |
| HA-MRSA 77090 (USA100/800) | 512/512/256/256/512 | 128/64/64 | 4/≤2/2 | ≤2/≤2/1 | 512/128/512 | 32/16/64 | 16/16/32 |
| VRSA 105 | 128/128/64/128/64 | 128/128/128/256 | 64/64/8/128 | 4/≤2/2/4 | 2048/1024/>512/>512 | 512/1024/256/>512 | 32/8/8/16 |
| VRSA 106 | 128/128/128 | 256/128 | 128/128 | 64/64 | 1024/1024 | 512/512 | 256/256 |
| VISA 92 | 2048/2048/2048 | 128/128 | 256/128 | 256/128 | 1024/1024 | 1024/1024 | 1024/512 |
| VISA 95 | 1024/1024/512/2048/1024 | 128/64/64 | 64/32/64 | 64/16/32 | 1024/512/512/512 | 512/256/256/512 | 512/64/64/256 |
| VISA 96 | 512/512/512 | 32/32 | 16/16 | 8/4 | 128/128 | 64/64 | 32/16 |

TABLE 7

Effect of Adding PEP35 15 Minutes Before or After Cephalosporins on Synergy versus CA-MRSA and HA-MRSA

| ORGANISM | PEP35 & CFZ Avg ΣFIC (range) | PEP35 & CFZ[a] Avg ΣFIC (range) | PEP35[b] & CFZ Avg ΣFIC (range) | PEP35 & CTR Avg ΣFIC (range) | PEP35 & CTR[c] Avg ΣFIC (range) | PEP35[d] & CTR Avg ΣFIC (range) |
|---|---|---|---|---|---|---|
| CA-MRSA 69615 (USA400) | 0.29 (0.12-0.53) 0.21 (0.045-0.515) | 0.29 (0.12-0.53) 0.21 (0.045-0.515) | 0.21 (0.045-0.508) | 0.26 (0.09-0.53) 0.26 (0.09-0.53) | 0.26 (0.09-0.53) 0.26 (0.09-0.53) | 0.24 (0.06-0.53) |
| CA-MRSA 70857 (USA400) | 0.21 (0.45-0.515) | 0.26 (0.09-0.53) | 0.23 (0.075-0.53) | 0.30 (0.12-0.53) | 0.34 (0.18-0.53) | 0.26 (0.09-0.53) |

TABLE 7-continued

Effect of Adding PEP35 15 Minutes Before or After Cephalosporins on Synergy versus CA-MRSA and HA-MRSA

| ORGANISM | PEP35 & CFZ Avg ΣFIC (range) | PEP35 & CFZ[a] Avg ΣFIC (range) | PEP35[b] & CFZ Avg ΣFIC (range) | PEP35 & CTR Avg ΣFIC (range) | PEP35 & CTR[c] Avg ΣFIC (range) | PEP35[d] & CTR Avg ΣFIC (range) |
|---|---|---|---|---|---|---|
| HA-MRSA 77090 (USA100/800) | 0.21 (0.045-0.515) 0.21 (0.045-0.53) | 0.19 (0.03-0.515) 0.18 (0.03-0.515) | 0.21 (0.045-0.53) | 0.23 (0.06-0.515) 0.26 (0.9-0.53) | 0.23 (0.06-0.515) 0.29 (0.12-0.53) | 0.21 (0.06-0.53) |
| HA-MRSA 70798 (USA 100/800) | 0.56 (0.028-1.015) | 0.56 (0.28-1.015) | 0.47 (0.24-1.008) | 0.33 (0.18-0.515) | 0.40 (0.28-0.56) | 0.44 (0.31-0.56) |

[a]CFZ added 15 minutes post PEP35 & organism exposure
[b]PEP35 added 15 minutes post CFZ & organism exposure
[c]CTR added 15 minutes post PEP35 & organism exposure
[d]PEP35 added 15 minutes post CTR & organism exposure

TABLE 8

Effect of Increasing Concentration of PEP35 or Adding PEP35 15 Minutes Before or After Vancomycin on Activity (MICs) Versus VRSA

| ORGANISM | PEP35 | VAN | VANCOMYCIN & PEP35 (8 ug/mL) | VANCOMYCIN & PEP35 (32 ug/mL) |
|---|---|---|---|---|
| VRSA 105 | 128 | 512 | 128 | 8 |
| VRSA 105[a] | | | 256 | 8 |
| VRSA 105[b] | | | 256 | 8 |
| VRSA 106 | 128 | 512 | 128 | 4 |
| VRSA 106[a] | | | 256 | 4 |
| VRSA 106[b] | | | 256 | 4 |

[a]VAN added 15 minutes post PEP35 & organism exposure
[b]PEP35 added 15 minutes post VAN & organism exposure

TABLE 9

Effect of Adding PEP35 15 Minutes Before or After Vancomycin on Synergy Versus VRSA

| ORGANISM | VAN & PEP35 Avg ΣFIC (range) | VAN & PEP35[a] Avg ΣFIC (range) | VAN & PEP35[b] Avg ΣFIC (range) |
|---|---|---|---|
| VRSA 105 | 0.27 (0.09-0.53) | 0.27 (0.09-0.53) | 0.36 (0.135-1.03) |
| VRSA 106 | 0.35 (0.09-1.015) | 0.35 (0.09-1.015) | 0.35 (0.09-1.015) |

[a]VAN added 15 minutes post PEP35 & organism exposure
[b]PEP35 added 15 minutes post VAN & organism exposure

TABLE 10

Effect of Increasing PEP35 Concentration on Activity (MICs) With and Without Vancomycin Versus MRSA, VISA and VRSA

| ISOLATE | VANCOMYCIN | VANCOMYCIN & PEP35 (8 ug/mL) | VANCOMYCIN & PEP35 (32 ug/mL) |
|---|---|---|---|
| MSSA 79333 | 1/0.5 | 1/1 | 1/1 |
| CA-MRSA 69615 (USA400) | 1/1 | 1/1 | 1/1 |
| HA-MRSA 77090 (USA100/800) | 1/1 | 1/1 | 1/1 |
| VRSA 105 | 512/512/512 | 16/256/128 | 4/4/8 |
| VRSA 106 | 512/512/512 | 32/32/128 | 4/4/4 |
| VISA 92 | 4/4 | 4/4 | 4/4 |
| VISA 95 | 2/4 | 2/2 | 2/2 |
| VISA 96 | 4/4 | 4/4 | 4/4 |

TABLE 11

Synergy studies with PEP35 against Gram-positive cocci with various antibiotics

| | | Cefazolin Avg ΣFIC (range) | Ceftriaxone Avg ΣFIC (range) | Daptomycin Avg ΣFIC (range) | Linezolid Avg ΣFIC (range) | Tigecycline Avg ΣFIC (range) | Vancomycin Avg ΣFIC (range) |
|---|---|---|---|---|---|---|---|
| Stock. | Organism | | | | | | |
| *S. pneumoniae*-Pen S n = 2 (MHB) | | | | | | | |
| 70400 | *Streptococcus pneumoniae* | 0.68 (0.515-1.06) | 0.99 (0.62-1.06) | 1.21 (1.03-1.5) | 0.63 (0.5-1.06) | 0.91 (0.62-1.12) | 0.91 (0.56-1.25) |
| 71263 | *Streptococcus pneumoniae* | 0.99 (0.62-1.25) | 0.91 (0.62-1.12) | 1.39 (1.03-2.5) | 0.92 (0.62-1.12) | 0.92 (0.56-1.25) | 1.05 (0.75-1.25) |
| *S. pneumoniae*-Pen I n = 2 (MHB) | | | | | | | |
| 72302 | *Streptococcus pneumoniae* | 1.1 (1.0-1.25) | 1.05 (0.75-1.25) | 0.99 (0.62-1.25) | 0.86 (0.56-1.12) | 0.68 (0.53-1.03) | 1.26 (1.06-1.5) |
| 78663 | *Streptococcus pneumoniae* | 1.1 (1.0-1.25) | 1.1 (1.0-1.25) | 1.19 (1.03-1.5) | 1.05 (0.75-1.25) | 1.0 (0.56-1.12) | 1.1 (1.0-1.25) |
| *S. pneumoniae*-Pen R n = 2 (MHB) | | | | | | | |
| 78519 | *Streptococcus pneumoniae* | 0.97 (0.75-1.12) | 1.05 (0.75-1.25) | 1.19 (1.03-1.5) | 0.92 (0.75-1.12) | 0.98 (0.75-1.12) | 1.2 (1.015-1.5) |
| 76065 | *Streptococcus pneumoniae* | 0.70 (0.53-1.06) | 1.21 (1.03-1.5) | 1.09 (0.56-1.5) | 0.74 (0.53-1.12) | 0.91 (0.62-1.12) | 0.86 (0.53-1.25) |
| MSSA-n = 2 (MH) | | | | | | | |
| 79333 | *Staphylococcus aureus* (2008) | 1.04 (0.75-1.25) | 0.86 (0.56-1.12) | 1.19 (1.03-1.5) | 1.05 (0.75-1.25) | 0.99 (0.62-1.5) | 1.11 (1.0-1.25) |
| 83424 | *Staphylococcus aureus* (2008) | 1.02 (0.75-1.25) | 0.80 (0.5-1.12) | 1.58 (1.015-2.5) | 0.74 (0.515-1.06) | 0.85 (0.5-1.12) | 1.19 (1.03-1.5) |
| CA-MRSA n = 2 (MH) | | | | | | | |
| 69615 | *Staphylococcus aureus*, MRSA | 0.27 (0.09-0.56) 0.24 (0.06-0.53) | 0.30 (0.12-0.53) 0.33 (0.18-0.53) | 1.18 (1.015-1.5) | 0.80 (0.515-1.12) | 0.93 (0.62-1.12) | 1.19 (1.03-1.5) |
| 70857 | *Staphylococcus aureus*, MRSA | 0.3 (0.12-0.56) 0.26 (0.09-0.53) | 0.51 (0.18-1.015) | 1.18 (1.015-1.5) | 0.89 (0.5-1.12) | 0.74 (0.5-1.06) | 1.05 (0.75-1.25) |
| HA-MRSA-n = 2 (MH) | | | | | | | |
| 77090 | *Staphylococcus aureus*, MRSA | 0.30 (0.12-0.56) 0.24 (0.075-0.53) | 0.27 (0.09-0.53) 0.27 (0.09-0.56) | 1.27 (1.015-2.03) | 0.74 (0.53-1.06) | 0.83 (0.5-1.12) | 0.95 (0.56-1.25) |
| 70798 | *Staphylococcus aureus*, MRSA | 0.30 (0.15-0.53) 0.54 (0.24-1.03) | 0.4 (0.265-0.56) 0.39 (0.15-1.015) | 0.99 (0.53-1.5) | 0.70 (0.5-1.06) | 0.77 (0.5-1.06) | 1.19 (1.03-1.5) |
| R&D STK# | Organism | | | | | | |
| VISA-n = 3 (MH) | | | | | | | |
| 92 | *S. aureus* Van Intermediate | 0.33 (0.18-0.53) 0.45 (0.18-1.015) | 0.52 (0.28-1.06) | 1.54 (1.015-2.5) | 0.99 (0.75-1.12) | 0.56 (0.31-1.06) | 1.1 (1.0-1.25) |
| 95 | *S. aureus* Van Intermediate | 0.49 (0.31-0.62) 0.37 (0.18-0.56) | 0.28 (0.09-0.56) 0.37 (0.18-0.56) | 1.23 (1.06-1.5) | 0.98 (0.62-1.25) | 0.46 (0.37-0.56) 0.43 (0.31-0.56) | 1.1 (1.03-1.25) |
| 96 | *S. aureus* Van Intermediate | 0.34 (0.18-0.56) 0.53 (0.31-1.03) | 0.31 (0.15-0.53) 0.47 (0.24-1.03) | 1.21 (1.03-1.5) | 0.77 (0.56-1.06) | 0.91 (0.62-1.12) | 0.88 (0.53-0.125) |
| VRSA-n = 2 (MH) | | | | | | | |
| 105 | *S. aureus* Van Resistant | 0.63 (0.5-1.015) | 0.45 (0.24-0.56) 0.54 (0.18-1.06) | 0.52 (0.37-0.62) | 0.80 (0.5-1.06) | 0.93 (0.62-1.12) | 0.3 (0.15-0.53) 0.49 (0.24-1.06) |
| 106 | *S. aureus* Van Resistant | 0.47 (0.265-1.06) 0.59 (0.31-1.03) | 0.34 (0.135-0.56) 0.73 (0.5-1.06) | 0.91 (0.56-1.25) | 0.83 (0.5-1.12) | 1.2 (0.56-2.12) | 0.27 (0.09-0.53) 0.40 (0.15-1.06) |
| Stock. | Organism | | | | | | |
| MRSE-n = 2 (MH) | | | | | | | |
| 79617 | *Staphylococcus epidermidis* (2008) | 0.88 (0.53-1.25) | 0.88 (0.53-1.25) | 1.19 (1.03-1.5) | 1.10 (0.56-1.5) | 1.19 (1.03-1.5) | 0.99 (0.62-1.25) |
| 83100 | *Staphylococcus epidermidis* (2008) | 0.52 (0.37-0.62) | 1.05 (0.75-1.25) | 1.1 (1.0-1.25) | 0.73 (0.515-1.12) | 1.21 (1.03-1.5) | 0.60 (0.31.12) rpt |
| *S. agalactiae*-n = 2 (MHB) | | | | | | | |
| 80870 | *Streptococcus agalactiae* (2008) | 0.92 (0.56-1.25) | 0.99 (0.53-1.25) | 0.83 (0.53-1.12) | 1.1 (1.0-1.25) | 1.10 (1.0-1.25) | 1.05 (0.75-1.25) |
| 81262 | *Streptococcus agalactiae* (2008) | 1.10 (1-1.25) | 1.05 (0.75-1.25) | 1.69 (1.06-2.5) | 0.91 (0.53-1.25) | 1.05 (0.75-1.25) | 1.1 (1.0-1.25) |
| *S. pyogenes*-n =2 (MHB) | | | | | | | |
| 77765 | *Streptococcus pyogenes* (2008) | 1.04 (0.75-1.25) | 1.19 (0.03-1.5) | 1.19 (1.03-1.5) | 1.05 (0.75-1.25) | 1.1 (1.0-1.25) | 1.09 (1.0-1.25) |

TABLE 11-continued

Synergy studies with PEP35 against Gram-positive cocci with various antibiotics

| | | Cefazolin Avg ΣFIC (range) | Ceftriaxone Avg ΣFIC (range) | Daptomycin Avg ΣFIC (range) | Linezolid Avg ΣFIC (range) | Tigecycline Avg ΣFIC (range) | Vancomycin Avg ΣFIC (range) |
|---|---|---|---|---|---|---|---|
| 79531 | *Streptococcus pyogenes* (2008) | 1.19 (1.03-1.5) | 1.19 (1.03-1.5) | 1.19 (1.03-1.5) | 1.19 (1.03-1.5) | 1.1 (1.0-1.25) | 1.27 (1.015-2.5) |
| *E. faecalis* n =2 (MH) | | | | | | | |
| 78145 | *Enterococcus faecalis* | 0.93 (0.62-1.06) | 0.72 (0.53-1.12) | 1.39 (1.03-2.25) | 0.88 (0.62-1.06) | 0.9 (0.5-1.12) | 1.19 (1.03-15) |
| 70468 | *Enterococcus faecalis* | 0.94 (0.56-1.25) | 1.1 (1-1.25) | 1.5 (1-2.25) | 0.99 (0.62-1.25) | 0.82 (0.5-1.06) | 1.1 (1-1.25) |
| *E. Faecium*-n = 2 (MH) | | | | | | | |
| 78024 | *Enterococcus faecium* | 1.16 (1.015-1.5) | >1* | 1.19 (1.03-1.5) | 1.1 (1-1.25) | 1.19 (1.03-1.5) | 1.19 (1.03-1.5) |
| 78352 | *Enterococcus faecium* | 1.10 (1-1.25) | 0.99 (0.62-1.25) | 1.10 (0.75-1.5) | 0.80 (0.5-1.06) | 0.99 (0.75-1.12) | 1.59 (1.06-2.5) |
| VRE-n =2 (MH) | | | | | | | |
| 70769 | *Enterococcus faecium* | >1* | >1* | 0.82 (0.28-1.25) | 1.09 (1-1.25) | 1.2 (1.03-1.05) | 0.92 (0.506-1.25) |
| 77872 | *Enterococcus faecium* | >1* | >1* | 1.34 (1.03-1.5) | 1.19 (1.03-1.5) | 1.39 (1.03-2.06) | 1.19 (1.03-1.5) |

TABLE 12

Synergy studies with PEP35 against Gram-negative cocci with various antibiotics

| Stock. | Organism | Gentamicin Avg ΣFIC (range) | Levofloxacin Avg ΣFIC (range) | Piperacillin/Tazobactam Avg ΣFIC (range) | Meropenem Avg ΣFIC (range) | Colistin Avg ΣFIC (range) |
|---|---|---|---|---|---|---|
| *E.coli* n =2 (MH) | | | | | | |
| 69716 | *Escherichia coli* | 1.4 (1.06-2.12) | 0.93 (0.56-1.12) | 0.63 (0.5-1.03) | 0.86 (0.53-1.25) | 0.71 (0.31-1.06) |
| 70752 | *Escherichia coli* | 1.05 (0.75-1.25) | 1.13 (0.75-1.12) | 0.63 (0.24-1.03) | 1.21 (1.03-1.5) | 0.81 (0.31-1.25) |
| *P. aeruginosa*-n =2 (MH) | | | | | | |
| 70849 | *Pseudomonas aeruginosa* | 1.11 (1.03-1.25) | 1.21 (1.03-1.5) | 0.92 (0.62-1.12) | 1.21 (1.03-1.5) | 0.70 (0.28-1.12) |
| 71841 | *Pseudomonas aeruginosa* | 1.05 (0.75-1.25) | 1.13 (1.0-1.25) | 0.88 (0.56-1.12) | 1.10 (1.0-1.25) | 0.89 (0.53-1.25) |
| *K. pneumoniae*-n =2 (MH) | | | | | | |
| 77081 | *Klebsiella pneumoniae* | 0.89 (0.56-1.25) | 1.14 (1.06-1.25) | 1.05 (0.75-1.25) | 1.21 (1.03-1.5) | 0.61 (0.18-1.06) |
| 70508 | *Klebsiella pneumoniae* | 1.13 (1.0-1.25) | 0.97 (0.75-1.12) | 0.93 (0.62-1.12) | 1.19 (1.03-1.5) | 0.67 (0.31-1.06) |
| *K. oxytoca*-n =2 (MH) | | | | | | |
| 76874 | *Klebsiella oxytoca* | 1.10 (0.75-2.06) | 0.94 (0.62-1.12) | 0.83 (0.53-1.12) | 0.80 (0.53-1.12) | 0.83 (0.31-2.03) |
| 75316 | *Klebsiella oxytoca* | 1.24 (0.75-2.12) | 0.88 (0.53-1.25) | 0.93 (0.62-1.12) | 1.1 (1.0-1.25) | 0.41 (0.24-0.56) |
| | | | | | | 0.62 (0.18-1.06) |
| | | | | | | 0.65 (0.18-1.12) |
| *E. cloacae*-n =2 (MH) | | | | | | |
| 80194 | *Enterobacter cloacae* (2008) | 1.4 (0.5-2.12) | 1.13 (1.0-1.25) | 0.79 (0.5-1.06) | 1.32 (1.03-2.12) | 0.70 (0.31-1.12) |
| 83128 | *Enterobacter cloacae* (2008) | 1.05 (0.75-1.25) | 0.98 (0.75-1.12) | 0.71 (0.37-1.06) | 1.05 (0.75-1.25) | 0.77 (0.5-1.06) |
| *P. mirabilis*-n =2 (MH) | | | | | | |
| 80267 | *Proteus mirabilis* (2008) | >1* | >1* | >0.5* | >1* | >1** |
| 81569 | *Proteus mirabilis* (2008) | >1* | >1* | >0.5* | >1* | >1** |
| *S. maltophilia*-n =2 (MH) | | | | | | |
| 73062 | *Stenotrophomonas maltophilia* | 1.4 (0.62-2.25) | 1.21 (1.03-1.5) | 0.98 (0.62-1.25) | 0.77 (0.5-1.03) | 0.88 (0.53-1.25) |
| 77424 | *Stenotrophomonas maltophilia* | 1.99 (1.0-4.25) | 0.94 (0.62-1.12) | 1.04 (0.75-1.25) | 1.05 (0.75-1.25) | 0.32 (0.18-0.53) |
| | | 1.98 (1.06-4.25) | | | | 0.92 (0.37-1.5) |
| | | | | | | 0.71 (0.37-1.06) |
| | | *PEP35 MIC > 4096 | *PEP35 MIC > 4096 | *PEP MIC > 4096 | *PEP MIC > 4096 | *PEP MIC > 4096 |
| | | | | | | ** PEP35 MIC > 4096 COL MIC > 4096 |

TABLE 13

Effect of Combining HybPEP35-1 and β-lactams on Activity (MICs) Versus CA-MRSA, HA-MRSA VISA and VRSA

| ISOLATE | hybPEP35 | Cefazolin | Cefazolin & hybPEP35 (32 ug/mL) | Ceftri-axone | Ceftriaxone & hybPEP35 (32 ug/mL) | Meropenem | Meropenem & hybPEP35 (32 ug/mL) | Piperacillin-Tazobactam | Pipercillin-Tazobactam & hybPEP35 (32 ug/mL) |
|---|---|---|---|---|---|---|---|---|---|
| MSSA 79333 | 128/128 | 0.5/0.5 | 0.5/≤0.25 | 4/4 | 2/2 | 0.25/0.12 | 0.12/0.06 | | |
| CA-MRSA 69615 (USA400) | 1024/1024 | 64/64 | 2/2 | 512/256 | 16/16 | 8/4 | 2/2 | | |
| CA-MRSA 70857 (USA400) | 1024/1024 | 32/32 | 2/2 | 256/128 | 16/16 | 4/4 | 2/2 | | |
| HA-MRSA 77090 (USA100/800) | 1024/512 | 256/256 | 8/16 | 1024/1024 | 64/64 | 32/32 | 8/16 | | |
| HA-MRSA 77098 (USA100/800) | ≥2048/2048 | 512/512 | 256/256 | 4096/4096 | 2048/2048 | 64/64 | 64/64 | | |
| VRSA 105 | 128/128 | 128/256 | 8/8 | 1024/1024 | 64/64 | 16/32 | 4/4 | | |
| VRSA 106 | 128/256 | 256/256 | 64/128 | 2048/2048 | 512/512 | 16/16 | 16/16 | | |
| VISA 96 | 1024/2048 | 64/32 | 4/8 | 256/256 | 32/32 | 8/8 | 4/4 | | |
| E. coli 69716 | 128/64 | | | | | | | 4/2 | ≤0.06/0.12 |
| E. coli 70752 | 64/64 | | | | | | | 4/4 | ≤0.06/≤0.06 |

TABLE 14

In Vitro Activity of Pep35 with and without Cefazolin or Cephalexin against CA-MRSA

| Organism | PEP35 | Cefazolin | Cefazolin & PEP35 32 ug/mL MIC * | Fold reduction | Cephalexin | Cephalexin & PEP35 32 ug/mL MIC * | Fold reduction |
|---|---|---|---|---|---|---|---|
| CA-MRSA (CMRSA7/USA400/MW2) | 512 | 64 | 1 | 64 | 256 | 16 | 16 |
| CA-MRSA (CMRSA7/USA400/MW2) | 512 | 128 | 2 | 64 | 512 | 64 | 8 |
| CA-MRSA (CMRSA7/USA400/MW2) | 512 | 128 | 2 | 64 | 512 | 64 | 8 |
| CA-MRSA (CMRSA7/USA400/MW2) | 512 | 128 | 2 | 64 | 512 | 64 | 8 |
| CA-MRSA (CMRSA7/USA400/MW2) | 512 | 8 | 1 | 8 | 128 | 8 | 16 |
| CA-MRSA (CMRSA7/USA400/MW2) | 512 | 64 | 2 | 32 | 256 | 64 | 4 |
| CA-MRSA (CMRSA7/USA400/MW2) | 256 | 8 | 1 | 8 | 128 | 8 | 16 |
| CA-MRSA (CMRSA7/USA400/MW2) | 512 | 256 | 2 | 128 | 256 | 64 | 4 |
| CA-MRSA (CMRSA7/USA400/MW2) | 512 | 64 | 2 | 32 | 256 | 64 | 4 |
| CA-MRSA (CMRSA7/USA400/MW2) | 512 | 128 | 2 | 64 | 512 | 64 | 8 |
| CA-MRSA (CMRSA7/USA400/MW2) | 512 | 64 | 2 | 32 | 256 | 64 | 4 |
| CA-MRSA (CMRSA7/USA400/MW2) | 512 | 64 | 1 | 64 | 256 | 32 | 8 |
| CA-MRSA (CMRSA7/USA400/MW2) | 512 | 64 | 2 | 32 | 256 | 64 | 4 |
| CA-MRSA (CMRSA7/USA400/MW2) | 512 | 64 | 2 | 32 | 256 | 32 | 8 |
| CA-MRSA (CMRSA10/USA300) | 512 | 64 | 2 | 32 | 256 | 32 | 8 |
| CA-MRSA (CMRSA10/USA300) | 512 | 128 | 2 | 64 | 512 | 64 | 8 |
| CA-MRSA (CMRSA10/USA300) | 512 | 64 | 2 | 32 | 256 | 32 | 8 |
| CA-MRSA (CMRSA10/USA300) | 512 | 128 | 2 | 64 | 256 | 64 | 4 |
| CA-MRSA (CMRSA10/USA300) | 256 | 128 | 2 | 64 | 512 | 64 | 8 |
| CA-MRSA (CMRSA10/USA300) | 512 | 128 | 2 | 64 | 256 | 64 | 4 |
| CA-MRSA (CMRSA10/USA300) | 1024 | 64 | 1 | 64 | 256 | 32 | 8 |
| CA-MRSA (CMRSA10/USA300) | 256 | 128 | 2 | 64 | 512 | 128 | 4 |
| CA-MRSA (CMRSA10/USA300) | 1024 | 128 | 2 | 64 | 512 | 128 | 4 |
| CA-MRSA (CMRSA10/USA300) | 1024 | 32 | 2 | 16 | 256 | 64 | 4 |
| CA-MRSA (CMRSA10/USA300) | 512 | 64 | 2 | 32 | 256 | 32 | 8 |
| CA-MRSA (CMRSA10/USA300) | 512 | 128 | 2 | 64 | 512 | 64 | 8 |
| CA-MRSA (CMRSA10/USA300) | 512 | 64 | 1 | 64 | 256 | 16 | 16 |
| CA-MRSA (CMRSA10/USA300) | 512 | 128 | 2 | 64 | 512 | 32 | 16 |
| CA-MRSA (CMRSA10/USA300) | 1024 | 128 | 2 | 64 | 256 | 64 | 4 |
| CA-MRSA (CMRSA10/USA300) | 512 | 64 | 2 | 32 | 256 | 64 | 4 |
| CA-MRSA (CMRSA10/USA300) | 512 | 4 | 1 | 4 | 128 | 8 | 16 |

TABLE 14-continued

In Vitro Activity of Pep35 with and without Cefazolin or Cephalexin against CA-MRSA

| Organism | PEP35 | Cefazolin | Cefazolin & PEP35 32 ug/mL MIC * | Fold reduction | Cephalexin | Cephalexin & PEP35 32 ug/mL MIC * | Fold reduction |
|---|---|---|---|---|---|---|---|
| CA-MRSA (CMRSA10/USA300) | 512 | 64 | 4 | 16 | 256 | 64 | 4 |
| CA-MRSA (CMRSA10/USA300) | 512 | 32 | 2 | 16 | 256 | 32 | 8 |
| CA-MRSA (CMRSA10/USA300) | 512 | 64 | 2 | 32 | 256 | 32 | 8 |
| CA-MRSA (CMRSA10/USA300) | 512 | 4 | 2 | 2 | 64 | 8 | 8 |
| CA-MRSA (CMRSA10/USA300) | 512 | 64 | 2 | 32 | 256 | 8 | 32 |
| CA-MRSA (CMRSA10/USA300) | 512 | 128 | 4 | 32 | 512 | 128 | 4 |
| CA-MRSA (CMRSA10/USA300) | 512 | 64 | 1 | 64 | 256 | 8 | 32 |
| CA-MRSA (CMRSA10/USA300) | 512 | 64 | 2 | 32 | 256 | 64 | 4 |
| CA-MRSA (CMRSA10/USA300) | 512 | 64 | 2 | 32 | 256 | 32 | 8 |
| CA-MRSA (CMRSA10/USA300) | 512 | 64 | 1 | 64 | 256 | 8 | 32 |
| CA-MRSA (CMRSA10/USA300) | 512 | 64 | 2 | 32 | 256 | 32 | 8 |
| CA-MRSA (CMRSA10/USA300) | 512 | 64 | 2 | 32 | 256 | 32 | 8 |
| CA-MRSA (CMRSA10/USA300) | 512 | 2 | 1 | 2 | 64 | 4 | 16 |
| CA-MRSA (CMRSA10/USA300) | 256 | 128 | 4 | 32 | 256 | 128 | 2 |
| CA-MRSA (CMRSA10/USA300) | 1024 | 64 | 2 | 32 | 256 | 32 | 8 |
| CA-MRSA (CMRSA10/USA300) | 512 | 64 | 2 | 32 | 256 | 32 | 8 |
| CA-MRSA (CMRSA10/USA300) | 256 | 64 | 1 | 64 | 256 | 16 | 16 |
| CA-MRSA (CMRSA10/USA300) | 512 | 64 | 2 | 32 | 256 | 32 | 8 |
| CA-MRSA (CMRSA10/USA300) | 512 | 128 | 4 | 32 | 256 | 128 | 2 |
| S. aureus | 512 | 0.5/0.5 | 0.5 | 0.5 | 4/8 | 2 | 2 |
| E. coli | 64 | 2/2 | 1 | 2 | 8/8 | 8 | 8 |

* MIC ≤ 8 ug/ml is considered susceptible to treatment
* MIC ≥ 32 ug/ml is considered resistant to treatment

TABLE 15

In Vitro Activity of Pep35 with and without Cefazolin or Cephalexin against HA-MRSA

| Organism | PEP35 | Cefazolin | Cefazolin & PEP35 32 ug/mL MIC * | Fold reduction | Cephalexin | Cephalexin & PEP35 32 ug/mL MIC * | Fold reduction |
|---|---|---|---|---|---|---|---|
| HA-MRSA (CMRSA1/USA600) | 256 | 128 | 8 | 16 | 256 | 128 | 2 |
| HA-MRSA (CMRSA2/USA100/800/NY) | 256 | 8 | 1 | 8 | 128 | 16 | 8 |
| HA-MRSA (CMRSA2/USA100/800/NY) | 512 | 256 | 4 | 64 | 512 | 128 | 4 |
| HA-MRSA (CMRSA2/USA100/800/NY) | 512 | 512 | 256 | 2 | >512 | 512 | ≥2 |
| HA-MRSA (CMRSA2/USA100/800/NY) | 512 | 128 | 2 | 64 | 256 | 32 | 8 |
| HA-MRSA (CMRSA2/USA100/800/NY) | 512 | 512 | 128 | 4 | 512 | 512 | 0 |
| HA-MRSA (CMRSA2/USA100/800/NY) | 512 | 128 | 2 | 64 | 512 | 64 | 8 |
| HA-MRSA (CMRSA2/USA100/800/NY) | 1024 | 512 | 256 | 2 | >512 | 512 | ≥2 |
| HA-MRSA (CMRSA2/USA100/800/NY) | 512 | 256 | 2 | 128 | 512 | 64 | 8 |
| HA-MRSA (CMRSA2/USA100/800/NY) | 1024 | 512 | 128 | 4 | 512 | 512 | 0 |
| HA-MRSA (CMRSA2/USA100/800/NY) | 512 | 256 | 2 | 128 | 512 | 16 | 32 |
| HA-MRSA (CMRSA2/USA100/800/NY) | 256 | 256 | 64 | 4 | 512 | 256 | 2 |
| HA-MRSA (CMRSA2/USA100/800/NY) | 128 | 512 | 8 | 64 | >512 | 256 | ≥4 |
| HA-MRSA (CMRSA2/USA100/800/NY) | 512 | 256 | 4 | 64 | 256 | 256 | 0 |
| HA-MRSA (CMRSA2/USA100/800/NY) | 256 | 256 | 1 | 256 | 256 | 16 | 16 |
| HA-MRSA (CMRSA2/USA100/800/NY) | 512 | 128 | 2 | 64 | 512 | 64 | 8 |
| HA-MRSA (CMRSA2/USA100/800/NY) | 128 | 32 | 1 | 32 | 256 | 16 | 16 |

TABLE 15-continued

In Vitro Activity of Pep35 with and without Cefazolin or Cephalexin against HA-MRSA

| Organism | PEP35 | Cefazolin | Cefazolin & PEP35 32 ug/mL MIC * | Fold reduction | Cephalexin | Cephalexin & PEP35 32 ug/mL MIC * | Fold reduction |
|---|---|---|---|---|---|---|---|
| HA-MRSA (CMRSA2/USA100/800/NY) | 512 | 256 | 8 | 32 | 512 | 128 | 4 |
| HA-MRSA (CMRSA2/USA100/800/NY) | 512 | 32 | 1 | 32 | 256 | 8 | 32 |
| HA-MRSA (CMRSA2/USA100/800/NY) | 512 | 32 | 2 | 16 | 256 | 64 | 4 |
| HA-MRSA (CMRSA2/USA100/800/NY) | 256 | 512 | 128 | 4 | 512 | 256 | 2 |
| HA-MRSA (CMRSA2/USA100/800/NY) | 512 | 128 | 2 | 64 | 512 | 128 | 1 |
| HA-MRSA (CMRSA2/USA100/800/NY) | 512 | 256 | 4 | 64 | 512 | 128 | 1 |
| HA-MRSA (CMRSA2/USA100/800/NY) | 1024 | 32 | 2 | 16 | 256 | 64 | 1 |
| HA-MRSA (CMRSA2/USA100/800/NY) | 256 | 256 | 64 | 4 | 512 | 256 | 2 |
| HA-MRSA (CMRSA2/USA100/800/NY) | 1024 | 256 | 64 | 4 | 512 | 256 | 2 |
| HA-MRSA (CMRSA2/USA100/800/NY) | 1024 | 512 | 256 | 2 | >512 | 512 | ≥2 |
| HA-MRSA (CMRSA2/USA100/800/NY) | 1024 | 4 | 1 | 4 | 128 | 32 | 4 |
| HA-MRSA (CMRSA2/USA100/800/NY) | 512 | 256 | 128 | 2 | 512 | 256 | 2 |
| HA-MRSA (CMRSA2/USA100/800/NY) | 256 | 256 | 16 | 16 | 512 | 256 | 2 |
| HA-MRSA (CMRSA2/USA100/800/NY) | 512 | 128 | 4 | 32 | 512 | 128 | 4 |
| HA-MRSA (CMRSA2/USA100/800/NY) | 512 | 256 | 8 | 32 | 512 | 128 | 4 |
| HA-MRSA (CMRSA2/USA100/800/NY) | 512 | 128 | 4 | 32 | 256 | 64 | 4 |
| HA-MRSA (CMRSA2/USA100/800/NY) | 256 | 256 | 16 | 16 | 512 | 256 | 2 |
| HA-MRSA (CMRSA2/USA100/800/NY) | 512 | 32 | 2 | 16 | 256 | 32 | 8 |
| HA-MRSA (CMRSA2/USA100/800/NY) | 512 | 512 | 256 | 20 | >512 | 512 | ≥2 |
| HA-MRSA (CMRSA2/USA100/800/NY) | 512 | 128 | 4 | 32 | 512 | 128 | 4 |
| HA-MRSA (CMRSA2/USA100/800/NY) | 512 | 32 | 8 | 4 | 512 | 128 | 4 |
| HA-MRSA (CMRSA2/USA100/800/NY) | 512 | 64 | 2 | 8 | 256 | 64 | 4 |
| HA-MRSA (CMRSA2/USA100/800/NY) | 256 | 256 | 8 | 32 | 512 | 128 | 4 |
| HA-MRSA (CMRSA2/USA100/800/NY) | 512 | 128 | 4 | 32 | 512 | 128 | 4 |
| HA-MRSA (CMRSA2/USA100/800/NY) | 512 | 64 | 2 | 32 | 256 | 64 | 4 |
| HA-MRSA (CMRSA6) | 512 | 256 | 64 | 4 | 256 | 256 | 0 |
| HA-MRSA (CMRSA6) | 512 | 512 | 256 | 2 | 512 | 256 | 2 |
| HA-MRSA (CMRSA3/6) | 256 | 256 | 64 | 64 | 256 | 256 | 0 |
| HA-MRSA (CMRSA3/6) | 512 | 256 | 256 | 0 | 512 | 512 | 0 |
| HA-MRSA (CMRSA5/USA500) | 512 | 2 | 1 | 2 | 256 | 8 | 32 |
| HA-MRSA (CMRSA8) | 1024 | 64 | 4 | 16 | 256 | 128 | 2 |
| HA-MRSA (CMRSA4/USA200) | 512 | 256 | 128 | 2 | 512 | 256 | 2 |
| HA-MRSA (CMRSA4/USA200) | 512 | 128 | 2 | 64 | 256 | 128 | 2 |
| S. aureus | 1024 | 0.5/0.5 | 0.5 | 0.5 | 4/4 | 2 | 4 |
| E. coli | 64 | 2/2 | 1 | 2 | 8/8 | 4 | 8 |

* MIC ≤ 8 ug/ml is considered susceptible to treatment
* MIC ≥ 32 ug/ml is considered resistant to treatment

The invention claimed is:

1. A method for the prevention or treatment of antibiotic resistant *S. aureus* infection or reinfection, comprising administering a therapeutically effective amount of a beta-lactam antibiotic and a hyaluronic acid binding peptide comprising the amino acid sequence SEQ ID NO: 2.

2. The method of claim 1 wherein the *S. aureus* is a methicillin resistant variant (MRSA), a vancomycin resistant variant (VRSA), or a vancomycin intermediate resistant variant (VISA).

3. The method of claim 1 wherein the beta-lactam antibiotic and the hyaluronic acid binding peptide are administered within 15 minutes of each other.

4. The method of claim 1 wherein the beta-lactam antibiotic is a cephalosporin.

5. The method of claim 1 wherein the cephalosporin is a first generation cephalosporin.

6. The method of claim 1 wherein the cephalosporin is a second, third, fourth or fifth generation cephalosporin.

7. The method of claim 4 wherein the cephalosporin is selected from the group consisting of: cefacetrile, Cefadroxil, Cephalexin, Cefaloglycin, Cefalonium, Cefaloridine, Cefalotin, Cefapirin, Cefatrizine, Cefazaflur, Cefazedone, Cefazolin, Cefradine, Cefroxadine, Ceftezole, Cefaclor, Cefonicid, Cefprozil, Cefuroxime, Cefuzonam, Cefmetazole, Cefotetan, Cefoxitin, Carbacephems, Cephamycins, Cefcapene, Cefdaloxime, Cefdinir, Cefditoren, Cefetamet, Cefixime, Cefmenoxime, Cefodizime Cefotaxime, Cefovecin, Cefpimizole, Cefpodoxime Cefteram, Ceftibuten, Ceftiofur, Ceftiolene, Ceftizoxime, Ceftriaxone, Cefoperazone, Ceftazidime, Oxacephems, Cefclidine, Cefepime, Cefluprenam, Cefoselis, Cefozopran, Cefpirome, Cefquinome, Oxacephems, Ceftobiprole, medocaril, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftaroline, Ceftioxide, and Cefuracetime.

8. The method of claim 1 wherein the antibiotic is selected from the group consisting of methicillin, vancomycin, meropenem, and piperacillin/tazobactam.

9. The method of claim 1 wherein the hyaluronic acid binding peptide consists of the amino acid sequence SEQ ID NO: 2.

10. A method of potentiating a beta-lactam antibiotic against antibiotic resistant *S. aureus* comprising administering a hyaluronic acid binding peptide, comprising the amino acid sequence SEQ ID NO: 2, with the beta-lactam antibiotic.

11. The method of claim 10 wherein the antibiotic resistant *S. aureus* is a methicillin resistant variant (MRSA), a vancomycin resistant variant (VRSA) or a vancomycin intermediate resistant variant (VISA).

12. The method of claim 10 wherein the beta-lactam antibiotic and the hyaluronic acid binding peptide are administered simultaneously or concurrently.

13. The method of claim 12 wherein the beta-lactam antibiotic and the hyaluronic acid binding peptide are for administration within 15 minutes of each other.

14. The method of claim 12 wherein the beta-lactam antibiotic is a cephalosporin.

15. The method of claim 14 wherein the cephalosporin is a first generation cephalosporin.

16. The method of claim 14 wherein the cephalosporin is a second, third, fourth or fifth generation cephalosporin.

17. The method of claim 14 wherein the cephalosporin is selected from the group consisting of: cefacetrile, Cefadroxil, Cephalexin, Cefaloglycin, Cefalonium, Cefaloridine, Cefalotin, Cefapirin, Cefatrizine, Cefazaflur, Cefazedone, Cefazolin, Cefradine, Cefroxadine, Ceftezole, Cefaclor, Cefonicid, Cefprozil, Cefuroxime, Cefuzonam, Cefmetazole, Cefotetan, Cefoxitin, Carbacephems, Cephamycins, Cefcapene, Cefdaloxime, Cefdinir, Cefditoren, Cefetamet, Cefixime, Cefmenoxime, Cefodizime, Cefotaxime, Cefovecin, Cefpimizole, Cefpodoxime, Cefteram, Ceftibuten, Ceftiofur, Ceftiolene, Ceftizoxime, Ceftriaxone, Cefoperazone, Ceftazidime, Oxacephems, Cefclidine, Cefepime, Cefluprenam, Cefoselis, Cefozopran, Cefpirome, Cefquinome, Oxacephems, Ceftobiprole, medocaril, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftaroline, Ceftioxide, and Cefuracetime.

18. The method of claim 12 wherein the antibiotic is selected from the group consisting of methicillin, vancomycin, meropenem, and piperacillin/tazobactam.

19. The method of claim 12 wherein the hyaluronic acid binding peptide consists of the amino acid sequence SEQ ID NO: 2.

20. A composition comprising a beta-lactam antibiotic and a hyaluronic acid binding peptide comprising the amino acid sequence SEQ ID NO: 2.

21. The composition of claim 20 wherein the beta-lactam antibiotic is a cephalosporin.

22. The composition of claim 21 wherein the cephalosporin is a first generation cephalosporin.

23. The composition of claim 21 wherein the cephalosporin is a second, third, fourth or fifth generation cephalosporin.

24. The composition of claim 21 wherein the cephalosporin is selected from the group consisting of: cefacetrile, Cefadroxil, Cephalexin, Cefaloglycin, Cefalonium, Cefaloridine, Cefalotin, Cefapirin, Cefatrizine, Cefazaflur, Cefazedone, Cefazolin, Cefradine, Cefroxadine, Ceftezole, Cofactor, Cefonicid, Cefprozil, Cefuroxime, Cefuzonam, Cefmetazole, Cefotetan, Cefoxitin, Carbacephems, Cephamycins, Cefcapene, Cefdaloxime, Cefdinir, Cefditoren, Cefetamet, Cefixime, Cefmenoxime, Cefodizime, Cefotaxime, Cefovecin, Cefpimizole, Cefpodoxime, Cefteram, Ceftibuten, Ceftiofur, Ceftiolene, Ceftizoxime, Ceftriaxone, Cefoperazone, Ceftazidime, Oxacephems, Cefclidine, Cefepime, Cefluprenam, Cefoselis, Cefozopran, Cefpirome, Cefquinome, Oxacephems, Ceftobiprole, medocaril, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftaroline, Ceftioxide, and Cefuracetime.

25. The composition of claim 20 wherein the antibiotic is selected from the group consisting of methicillin, vancomycin, meropenem, and piperacillin/tazobactam.

26. The composition of claim 20 wherein the hyaluronic acid binding peptide consists of the amino acid sequence SEQ ID NO: 2.

27. The method of claim 2, wherein the combination of the hyaluronic acid binding protein with the antibiotic reduces the minimum inhibitory concentration of the MRSA strain.

28. The method of claim 2, wherein the combination of the hyaluronic acid binding protein with the antibiotic reduces the minimum inhibitory concentration of the MRSA strain 2-256 fold.

29. The method of claim 2, wherein the combination of the hyaluronic acid binding protein with the antibiotic reverts the minimum inhibitory concentration of the MRSA strain to susceptible (≤8 ug/mL).

* * * * *